US012590100B2

(12) United States Patent
Cuadrado Pastor et al.

(10) Patent No.: US 12,590,100 B2
(45) Date of Patent: Mar. 31, 2026

(54) TETRAHYDRO-SPIROINDOLINE-PYRROLOPYRROLE-TRIONES INHIBITORS OF THE NRF2-β-TRCP INTERACTION FOR USE IN THE TREATMENT OF FATTY LIVER DISEASE

(71) Applicants: Universidad Autonoma De Madrid, Madrid (ES); Consejo Superior De Investigaciones Cientificas, Madrid (ES); Universidad Miguel Hernandez De Elche, Alicante (ES); Fundacion De Investigacion Biomedica Del Hospital Universitario De La Princesa, Madrid (ES)

(72) Inventors: Antonio Cuadrado Pastor, Madrid (ES); Raquel Fernandez Gines, Madrid (ES); Jose Antonio Encinar, Elche (ES); Rafael Leon Martinez, Madrid (ES); Juan Felipe Franco Gonzalez, Madrid (ES); Manuela Garcia Lopez, Madrid (ES); Maria Isabel Rodriguez Franco, Madrid (ES); Ana Isabel Rojo Sanchis, Madrid (ES)

( * ) Notice: Subject to any disclaimer, the term of this patent is extended or adjusted under 35 U.S.C. 154(b) by 310 days.

(21) Appl. No.: 18/027,990

(22) PCT Filed: Jan. 13, 2022

(86) PCT No.: PCT/EP2022/050657
§ 371 (c)(1),
(2) Date: Mar. 23, 2023

(87) PCT Pub. No.: WO2022/152800
PCT Pub. Date: Jul. 21, 2022

(65) Prior Publication Data

US 2023/0348482 A1 Nov. 2, 2023

(30) Foreign Application Priority Data

Jan. 15, 2021 (EP) .................................... 21382025

(51) Int. Cl.
*C07D 487/20* (2006.01)
*A61P 1/16* (2006.01)
*G01N 33/50* (2006.01)

(52) U.S. Cl.
CPC .............. *C07D 487/20* (2013.01); *A61P 1/16* (2018.01); *G01N 33/5008* (2013.01)

(58) Field of Classification Search
CPC ...... C07D 487/20; A61P 1/16; G01N 33/5008
USPC .......................................................... 514/409
See application file for complete search history.

(56) References Cited

FOREIGN PATENT DOCUMENTS

| | | |
|---|---|---|
| CN | 105412089 | 6/2018 |
| WO | 2016201440 | 12/2016 |
| WO | 2020160010 | 8/2020 |

OTHER PUBLICATIONS

Moreno et al Antioxidants 2020, 9, 980 (Year: 2020).*
International Search Report and Written Opinion based on International Application Serial No. PCT/EP2022/050657, dated Apr. 20, 2022, pp. 1-13.
European Search Report based on co-pending European Patent Application No. 21382025.1 dated Jul. 2, 2021, pp. 1-13.
Rivera-Perez, Wbeimar, Andrey, et al., "Molecular Docking and In Silico Studies of the Physiochemical Properties of Potential Inhibitors for the Phosphotransferase System of *Streptococcus mutans*", Archives of Oral Biology, vol. 98, Feb. 1, 2019, pp. 164-175.
Damale, Manoj G., et al., "Molecular Docking, Pharmacophore Based Virtual Screening and Molecular Dynamics Studies Towards the Identification of Potential Leads for the Management of H. Pylori", RSC Advances, Aug. 21, 2019, vol. 9, No. 45, pp. 26176-26208.
Suymka, Ye I. et al. "Synthesis and the Antimicrobial Activity of Hexamethylene-N-Maleinimidospiroindole-3, 3'-Pyrrolo [3,4-c] Pyrrole Derivatives", Zhurnal Organichnoi Ta Farmatsevtichnoi Khimi, Dec. 14, 2017, vol. 15, Issue 4 (60), pp. 56-62.
Premachandra, Ilandari Dewage Udara Anulal, et al., "Potent Synergy Between Spirocyclic Pyrrolidinoindolinones and Fluconazole Against Candida Albicans", Chemmedchem Communications, Aug. 12, 2015, vol. 10, No. 10, pp. 1672-1686.
Guo, Rong, et al., "Discovery of ERBB3 Inhibitors for Non-Small Cell Lung Cancer (NSCLC) via Virtual Screening", Journal of Molecular Modeling, May 17, 2016, vol. 22, No. 6, pp. 1-9.
Zhang, Yongtao, et al., "Isorhynchophylline Enhances Nrf2 and Inhibits MAPK Pathway in Cardiac Hypertrophy", Naunyn-Schmiedeberg's Archives of Pharmacology, Sep. 5, 2019, vol. 393, No. 2, pp. 203-212.
Zhang, Donna D., et al., "The Role of Natural Products in Revealing NRF2 Function", Natural Product Reports, Jun. 24, 2020, vol. 37, No. 6, pp. 797-826.
Zhang, Di, et al., "Abstract C063: A Novel Nrf2 Inhibitor Suppresses Proliferation and Enhances the Sensitivity of Cancer Cells to Chemotherapy", AACR-NCI-EORTC International Conference on Molecular Targets and Cancer Therapeutics, Oct. 26, 2019, p. C063—2 Pages.
Choi, E-J, et al., "A Clinical Drug Library Screen Identifies Clobetasol Propionate as an NRF2 Inhibitor with Potential Therapeutic Efficacy in KEAP1 Mutant Lung Cancer", Oncogene, Sep. 1, 2017, vol. 36, No. 37, pp. 5285-5295.
Gunne, Sandra, et al., "Nrf2-A Molecular Target for Sepsis Patients in Critical Care", Biomolecules, Dec. 17, 2020, vol. 10, No. 12, pp. 1-22.

* cited by examiner

*Primary Examiner* — Yevgeny Valenrod
(74) *Attorney, Agent, or Firm* — McCarter & English, LLC

(57) ABSTRACT

The present invention relates to NRF2-βTrCP interaction inhibitors with general formula I and its derivate salts for use in the treatment of NRF2-related diseases caused by chronic inflammation and oxidative stress. More specifically the present invention relates to NRF2-βTrCP interaction inhibitors with specific formula I and its derivate salts for treating diseases of the liver related with chronic inflammation and oxidative stress, such as fatty liver disease.

3 Claims, 22 Drawing Sheets

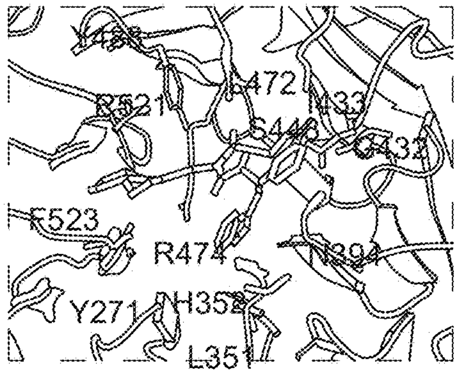
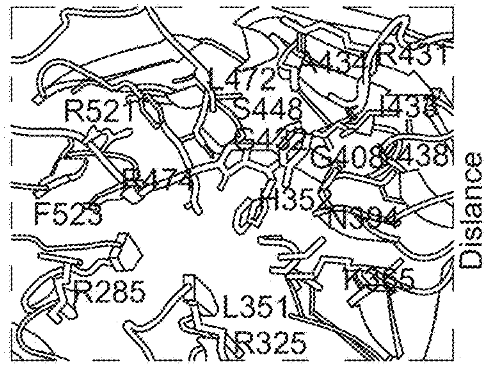
β- TrCP ΔG= -10.35 kcal/mol
FIG. 3A
FIG. 3B
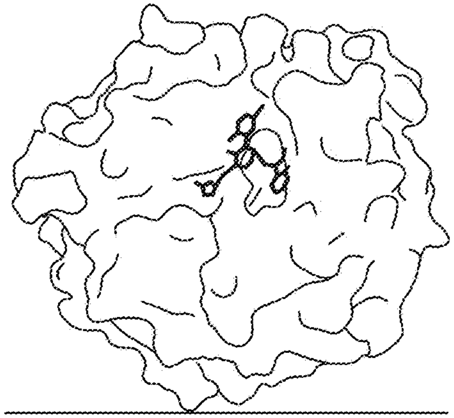
t=100ns
FIG. 3C
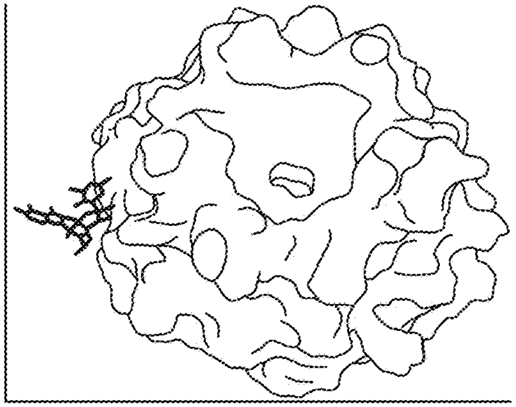
t=100ns
FIG. 3D
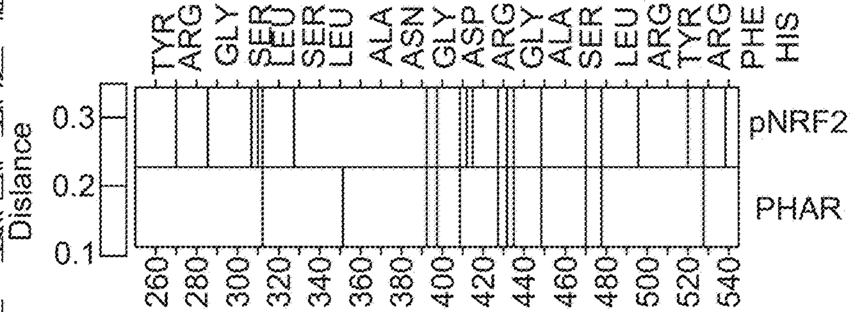
FIG. 3E
| MW | Total Surface Area | Polar Surface Area |
| --- | --- | --- |
| 554.989 | 374.03 | 112.76 |
| H-Acceptors | H-Donore | Rotable bonds |
| 9 | 3 | 3 |
| cLogS | cLogP | Ro5 violations |
| -6.305 | 2.982 | 0 |
| BBB | Caco-2 permead. | HIA |
| BBB- | | HIA+ |
FIG. 3F Vehicle PHAR LPS LPS+PHAR

H&E

F4/80

TETRAHYDRO-SPIROINDOLINE-PYRROLOPYRROLE-TRIONES INHIBITORS OF THE NRF2-β-TRCP INTERACTION FOR USE IN THE TREATMENT OF FATTY LIVER DISEASE

FIELD OF THE INVENTION

The present invention refers to the medical field. Particularly, the present invention relates to NRF2-βTrCP interaction inhibitors which lead to a moderate increase in NRF2 levels, within the physiological range. These molecular disrupters are used, according to the present invention, in the treatment of NRF2-related diseases that present with chronic inflammation and oxidative stress, comprising liver disease, preferably fatty liver disease.

STATE OF THE ART

Inflammatory response plays an important role in the pathology of most diseases, including liver damage, which lead to a progressive deterioration of metabolic functions. In clinical practice, there is a large number of non-steroidal anti-inflammatory drugs (NSAIDs) for alleviating pain and inflammation. However, NSAIDs have adverse side effects whose risk of onset is higher the higher the dose and/or the longer the duration over time. Irritation of the digestive tract, hepatotoxicity, high blood pressure, fluid retention, kidney problems, heart problems, and/or rashes are included among the unwanted side effects which may occur.

There is therefore an unmet medical need to find other compounds that may perform an anti-inflammatory and cytoprotective function without exhibiting the side effects described in the preceding paragraph, particularly in the treatment of NRF2-related diseases that present with chronic inflammation and oxidative stress, comprising liver disease, preferably fatty liver disease.

Precisely for the purpose of solving this technical problem, compounds with these properties have been developed in the present invention based on the activation of NRF2 (nuclear factor (erythroid-derived 2)-like 2) transcription factor by means of a completely novel technique consisting of interrupting its interaction with the E3 ligase adaptor protein referred to as β-TrCP (beta-transducin repeat-containing E3 ubiquitin protein ligase). Contrary to other strategies that activate NRF2, the targeted disruption of the NRF2/βTrCP interaction results in a moderate induction of its homeostatic functions in the range of physiological activity.

DESCRIPTION OF THE INVENTION

Brief Description of the Invention

As indicated above, the present invention relates to NRF2-βTrCP interaction inhibitors for use in the treatment of NRF2-related diseases (see FIG. 1) which show chronic inflammation and oxidative stress, comprising liver disease, preferably fatty liver disease. The protein βTrCP binds to NRF2 and sends it to degradation by the ubiquitin/proteasome pathway. The compounds of the present invention prevent this interaction and, therefore, the degradation of NRF2 through this pathway is prevented, giving rise to maintenance of their functional levels and their homeostatic activity. Importantly, this invention is not connected with the widely studied alternative for the degradation of NRF2, based on its binding with KEAP1. This invention is different in two respects: a) this invention refers to the disruption of NRF2/βTrCP which is a different mechanism to the KEAP1/NRF2, and b) the molecules object of this invention induce a gentler activation of NRF2 in comparison with the already described inhibitors of KEAP1/NRF2. This is of special interest because KEAP1/NRF2 inhibitors lead to a supra-physiological excess of NRF2 activation that can trigger possible unwanted effects.

Therefore, the first aspect of the present invention relates to NRF2-βTrCP interaction inhibitors, wherein the inhibitor can be optionally characterized by Formula (I), or its derivative salts,

I

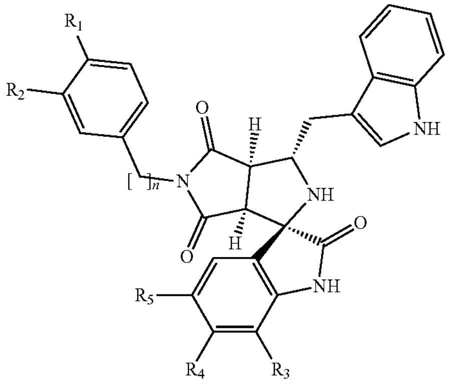

wherein:

n can be 0 or 1, $R_1$ can be $O_2CCH_3$ or a six-membered ring for forming a benzodioxane, benzomethylenedioxy, or naphthalene substituent;

$R_2$ can be H or a six-membered ring for forming a benzodioxane, benzomethylenedioxy, or naphthalene substituent;

$R_3$ can be H or $CH_3$;

$R_4$ can be H or $CH_3$; and $R_5$ can be H, Cl, or $CH_3$.

for use in the treatment of fatty liver disease. This invention is thus particularly focused on the treatment of liver diseases associated with low-grade chronic inflammation and its impact on the development of fatty liver and progression to fibrosis and cirrhosis.

In a preferred aspect of the invention, the NRF2-βTrCP interaction inhibitor is characterized by Formula (II) (hereinafter also referred to as PHAR),

II

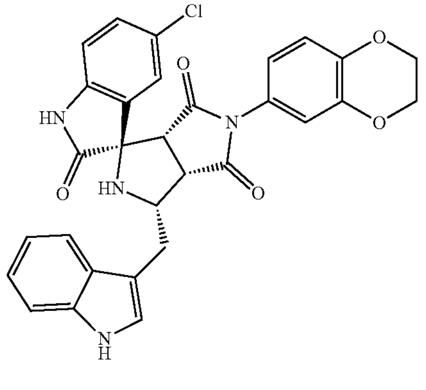

or its derivative salts.

The second aspect of the present invention relates to a pharmaceutical composition comprising the NRF2-βTrCP interaction inhibitor of Formula I or II, or derivative salts thereof, and optionally pharmaceutically acceptable vehicles or excipients, for use in the treatment of fatty liver disease. Alternatively, the present invention relates to a method for the treatment of fatty liver disease comprising the administration of a therapeutically effective dose or amount of a pharmaceutical composition comprising the NRF2-βTrCP interaction inhibitor of Formula I or II, or derivative salts thereof.

The third aspect of the present invention relates to an in vitro method for identifying and producing compounds for the treatment of fatty liver disease, which comprises: a) determining if the inhibition of NRF2-βTrCP interaction by the candidate compound has taken place, and b) wherein if the inhibition of NRF2-βTrCP interaction has taken place, it is indicative of the selected compound being effective in the treatment of fatty liver disease.

Different approaches have been used to determine if the compound inhibits NRF2-βTrCP interaction:

1. In vitro kinase assay and in vitro ubiquitination. For the recognition and degradation of NRF2 by βTrCP, the serines 335, 338, 342 and 347 located at the Neh6 domain of NRF2 need to be previously phosphorylated by the kinase GSK-3β (FIG. 1). Therefore, to obtain the phosphorylated substrate, 20 ng recombinant NRF2-DETGE was used together with 0.5 μg of recombinant GSK-3β incubated at 30° C. for 60 min. The result was analyzed by western blot. After confirming the existence of phosphorylation in the residues of interest, an in vitro ubiquitination assay was carried out using the recombinant proteins that make up the E3 ubiquitin ligase complex. The ubiquitination reaction was carried out using: ATP (2 mM), ubiquitin (30 mM), E1 (1 mM), Cdc34b (5 mM), SCF-βTrCP (450 nM), and non-phosphorylated or phosphorylated NRF2 (20 ng), in a specific ubiquitination buffer (30 mM Tris pH 7.6, 5 mM MgCl2, 2 mM dithiothreitol, 100 mM NaCl). Before the ubiquitination reactions, the E1, Cdc34b, and ubiquitin components were incubated together for 2 min to allow the E2 thioester bond to form. The reactions were incubated for 1 hour at 25° C. in the presence or absence of PHAR (3 μM) in order to determine whether or not PHAR inhibits ubiquitination by βTrCP. The result was that indeed PHAR prevents the ubiquitination of NRF2.
2. The PI3K/AKT signaling pathway is inhibited, and therefore GSK-3β is activated with the PI3K inhibitor, LY294002. As a result, NRF2 is phosphorylated by GSK-3β and marked for degradation by means of interaction with β-TrCP. Therefore, if PHAR is capable of inhibiting βTrCP-NRF2 interaction, the NRF2 levels will remain stable independently of the activation and phosphorylation by GSK-3β. The obtained result corroborates this.
3. Using lentiviral silencing of the two isoforms described for β-TrCP (β-TrCP1 and β-TrCP2) in MEFs originating from Keap1 knockout mice (Keap'1−/−). Even though the silencing achieved was not 100%, NRF2 and HO-1 induction was considerably lower in βTrCP-silenced cells compared with shCTRL cells.

The following terms are defined for a better interpretation of the present invention:

The term "fatty liver disease" refers to a condition where excess fat builds up in the liver. Complications may include cirrhosis, liver cancer, and esophageal varices. There are two main types of fatty liver disease: non-alcoholic fatty liver disease (NAFLD) and alcoholic liver disease (ALD). NAFLD is made up of simple fatty liver and non-alcoholic steatohepatitis (NASH). The primary risks include alcohol, type 2 diabetes, and obesity. Other risk factors include certain medications such as glucocorticoids, and hepatitis C. Some people with NAFLD develop simple fatty liver and others develop NASH.

The term "comprising" means including but not limited to what follows the word "comprising". Therefore, the use of the term "comprising" indicates that the listed elements are compulsory, but that other elements are optional and may or may not be present.

"Consists of" is understood as including and not limited to everything following the phrase "consists of". Therefore, the phrase "consists of" indicates that the listed elements are compulsory, and that there can be no other elements present.

"Therapeutically effective dose or amount" is understood as the amount which, when administered as described herein, produces a positive therapeutic response in a subject suffering from the disease. The exact amount required will vary from one subject to another, depending on the age and general condition of the subject, the severity of the condition being treated, the mode of administration, and the like. A suitable "effective" amount in any individual case can be determined by a person skilled in the art using routine experimentation, based on the information provided herein.

DESCRIPTION OF THE FIGURES

FIG. 3. PHAR binds specifically to βTrCP but not to KEAP1. A) and B), structure of the β-TrCP complex (PDB: 1P22) with the lowest free energy PHAR conformation. The figures illustrate the β-TrCP moieties participating in hydrophobic or electrostatic intermolecular interactions, respectively, with pNRF2, compared with the moieties for interaction with PHAR. β-TrCP is shown in a representation referred to as cartoon. Color code: Yellow: specific moieties for pNRF2/β-TrCP interaction; magenta: specific moieties for PHAR/β-TrCP interaction; blue: moieties shared between PHAR/pNRF2 and β-TrCP. C) and D), molecular dynamics simulations of PHAR with respect to β-TrCP and KEAP1 proteins, respectively, at a study time of 100 ns. β-TrCP and KEAP1 are shown in surface representation. E), map showing the interaction of β-TrCP moieties which interact with pNRF2 and/or PHAR throughout the 100 ns of the molecular dynamics simulation. The distance of interaction is represented by a color code in which black corresponds with the closest moieties and yellow the farthest ones. F), chemical absorption, distribution, metabolism, excretion, and toxicity (ADMET) properties of PHAR. MW: molecular weight; H-Acceptors: hydrogen bond acceptors; H-Donors: hydrogen bond donors; cLogS: estimated log (base 10) of solubility measured in mol/L; cLogP: estimated log (base 10) of n-octanol/water partition coefficient; Ro5violations: violations of Lipinski's rule of five; BBB: blood-brain barrier permeation capacity; Caco-2 permeab.: Caco-2 permeability; and HIA: human intestinal absorption was calculated using the web application DataWarrior and the ADMETsar online tool.

DETAILED DESCRIPTION OF THE INVENTION

The present invention is illustrated by means of the following examples without the intention of limiting the scope of protection of the invention.

Example 1. Result

Example 1.1. Computational Search for β-TrCP/NRF2 Interaction Inhibitors

Figure 1:
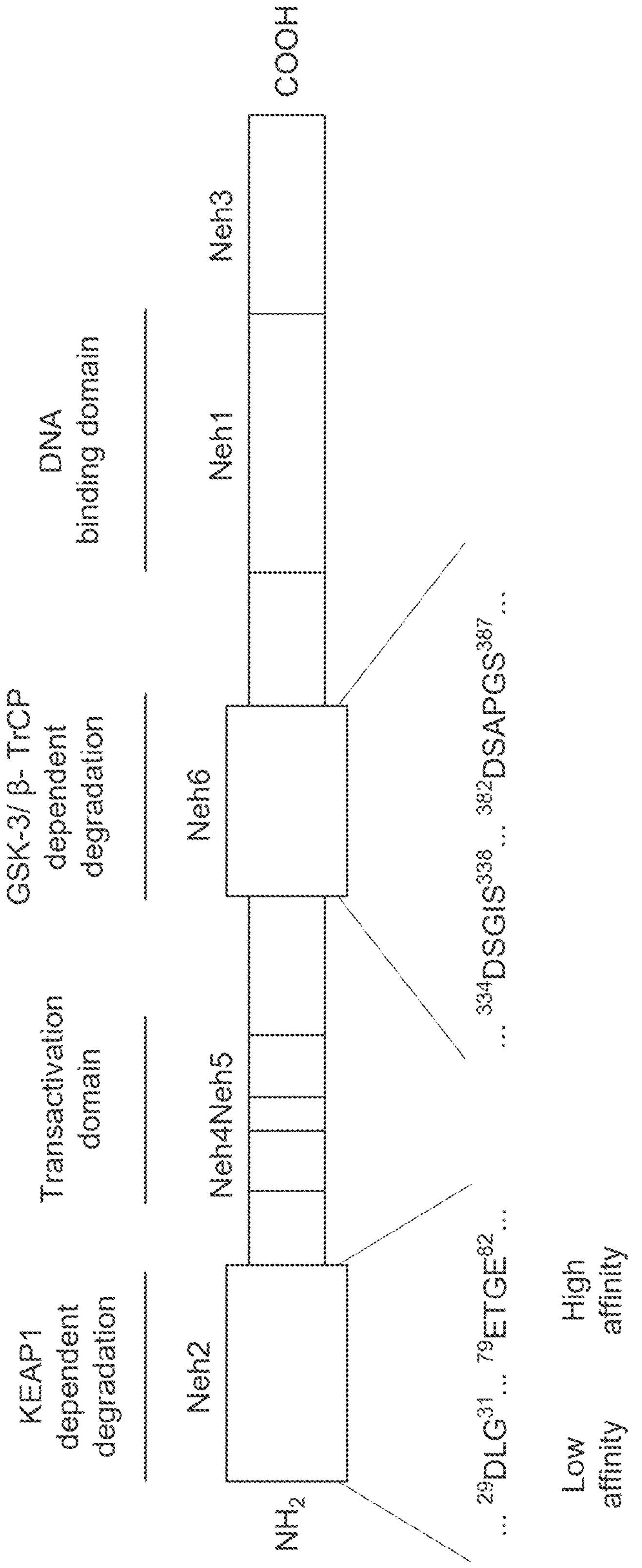
FIG. 1. NRF2 structure. The different NRF2 domains are shown. To provide a general view. The low affinity and high affinity motifs recognized by KEAP1 for interacting with NRF2 are shown in the Neh2 domain but are not the object of this invention. The moieties for GSK-3β interaction and the phosphorylation sites of (a) priming kinase(s) which is/are unknown at present are shown in the Neh6 domain, and this is the area of activity of our disrupter of the interaction between NRF2 and βTrCP.
Figure 2:
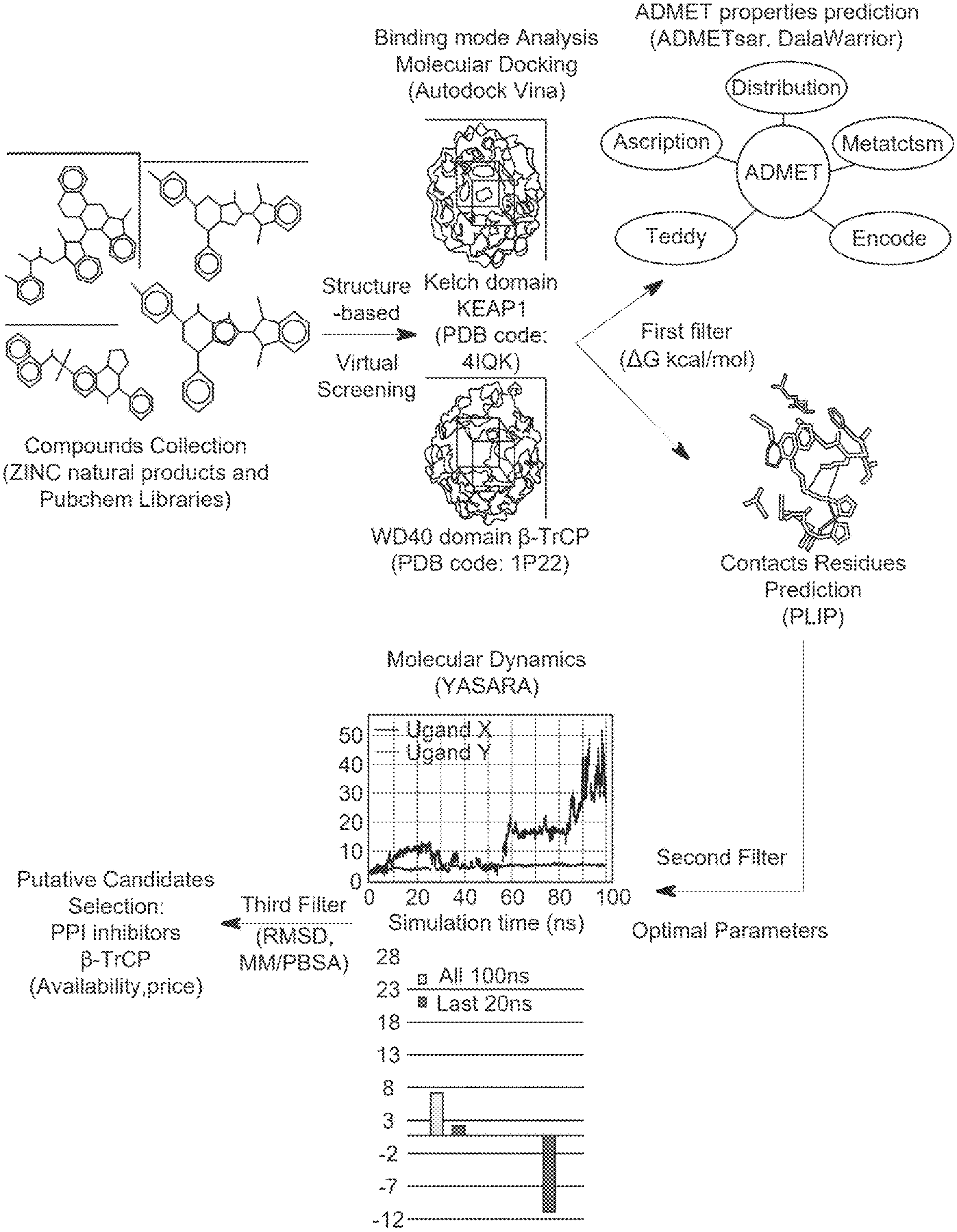
FIG. 2. Computational methodology carried out in this study. Diagram of the experiment carried out for identifying new candidate β-TrCP and NRF2 protein-protein interaction inhibitors.

In order to find molecules capable of specifically interrupting β-TrCP-NRF2 interaction, a virtual analysis was carried out by means of molecular modeling and molecular dynamics tools based on the structural similarity of 388,503 natural compounds obtained from the "ZINC natural products" and the "National Center for Biotechnology Information (NCBI) PubChem database" compound libraries (FIG. 2).

For this in silico study, the crystallographic structure PDB:1P22 of β-TrCP which is published in the Protein Data Bank database and complexed with Skp1-β-Catenin was used. The specific 3D preparation and editing of β-TrCP was performed using the tool Pymol software v 2.3.3, thereby obtaining the Skp1- and β-catenin-free β-TrCP molecule. The present group has previously characterized the most relevant moieties at the site of interaction between β-TrCP WD40 domain and the phosphodegron generated by GSK-3β in the Neh6 domain of NRF2. This NRF2 interaction site was used to identify the compounds having the highest theoretical affinity for β-TrCP. In this study, the AutoDock Vina tool which incorporates evolutionary and Lamarckian genetic algorithm methods, among others, has been used, allowing ligand flexibility to be modeled, while the receptor is kept rigid. Moreover, in addition to its theoretical efficacy for inhibiting β-TrCP-NRF2 interaction, ADMET properties (absorption, biodistribution, the speed at which it is metabolizes, excretion, and toxicity) were analyzed using DataWarrior software and the ADMETsar online tool.

Based on the data obtained from molecular modeling, 215 compounds were selected based on their Gibbs free energy (ΔG), meeting the criterion of ≤−9.5 kcal/mol. Then, those compounds with ADMET properties outside the established optimal ranges were eliminated. Lastly, due to the high structural homology among the 86 selected candidates, they were grouped into 39 clusters having at least 70% homology.

Since molecular modeling by AutoDock Vina only provides a static idea of interaction, to fine tune the selection of the best theoretical candidates, theoretical models of molecular dynamics are carried out using YASARA software. The purpose is to check whether the interactions established by the compounds selected in the first part of the process with β-TrCP are stable during the specific study time (100 ns). Based on these results, 4 candidates (representing 4 clusters having a different homology) with the theoretical capacity to establish stable interactions with β-TrCP throughout the study time were obtained.

By analyzing the computational parameters obtained for PHAR (FIG. 3), the molecular modeling results showed that the compound binds to β-TrCP with a theoretical value of ΔG=−10.35 kcal/mol. Using the PHAR pose with the lowest free energy derived from molecular modeling, the interactions established by the compound with β-TrCP moieties were studied in detail, establishing as selection criterion a distance less than or equal to 3.5 Å (FIGS. 3A and 3B). The purpose was to enable evaluating the capacity of the compound to interrupt β-TrCP-phospho-NRF2 (pNRF2) interactions. The β-TrCP moieties of interest involved in the hydrophobic interactions with pNRF2 are: Arg521, Phe523, Tyr271, Arg474, Ala 434, Asn394, and Leu351. Meanwhile, the electrostatic interactions involve the following β-TrCP moieties: Arg285, Ser325, Lys365, Tyr438, Arg431, Asn394, and Gly408. As shown in FIG. 3A, PHAR establishes interaction with most of the moieties involved in the hydrophobic pNRF2-β-TrCP interaction, with the exception of Tyr271. In contrast, only interaction with Ser448, involved in electrostatic interactions, could be inhibited by PHAR. It must be pointed out that PHAR is capable of establishing interaction with more β-TrCP moieties other than those listed above (magenta, FIGS. 3A and 3B). This could entail the advantage of taking up more space at the site where it interacts with pNRF2, complicating the binding capacity thereof.

In turn, as shown in FIG. 3C, the analysis of molecular dynamics showed that the interaction with β-TrCP, established by PHAR, is stable for at least 100 ns. In contrast, FIG. 3D shows how the interaction it establishes with KEAP1 is unstable since the compound leaves the binding site during this time. Again, long-term analysis of interacting moieties corroborated, by means of molecular dynamics, that PHAR interacts with many of the moieties involved in pNRF2/β-TrCP interaction such as: Asn394, Gly408, Arg431, Gly432, Ser448, Leu472, Arg474, Phe523 (FIG. 3E). With respect to ADMET predictions (FIG. 3F), PHAR is within the optimal ranges corresponding to Lipinski's rule.

Therefore, computational analysis shows that PHAR could indeed interact with β-TrCP, but not with KEAP1, in the key moieties of the NRF2 binding site, and could thereby compete with the binding of NRF2 to β-TrCP.

Example 1.2. PHAR Activates the NRF2-Mediated Signaling Pathway

Figure 4A:
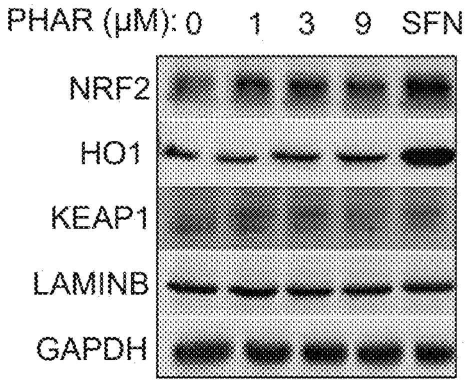
FIG. 4. PHAR activates the NRF2 pathway. MEFs in serum-depleted conditions were subjected to (A-C) 1 μM, 3 μM, or 10 μM of PHAR and 10 μM of SFN as a positive control for 16 h; or (D-F) 10 μM of PHAR for the indicated times. In both experiments, 0.1% DMSO was used as a vehicle. A), representative immunoblots of NRF2, HO1, KEAP1, LAMINB, and GAPDH as loading controls. B) and C), densitometric analysis of NRF2 and HO1 protein levels of the representative immunoblots depicted in (A), expressed as a ratio of NRF2/LAMINB or HO1/GAPDH. The data is depicted as means±SEM (n=3). Statistical analysis was performed with one-way ANOVA followed by the Bonferroni test to check inter-group differences. *$p<0.05$; ***$p<0.001$ vs. 0. D), representative immunoblots of NRF2, HO1, KEAP1, LAMINB, and GAPDH as loading controls. E) and F), Densitometric analysis of NRF2 and HO1 protein levels of the representative immunoblots of (D), expressed as a ratio of NRF2/LAMINB or HO1/GAPDH. The data is depicted as means±SEM (n=3). Statistical analysis was performed with one-way ANOVA followed by the Bonferroni test to check inter-group differences. *$p<0.05$; *$p<0.001$ vs. 0. G), Reporter MCF-7 c32 ARE-luc cells were subjected to 1 μM, 3 μM, or 9 μM of PHAR and 10 μM of SFN as a positive control. 0.1% DMSO was used as a vehicle. Luciferase activity was measured after 16 h of treatment. The data is depicted as means±SEM (n=3). Statistical analysis was performed with one-way ANOVA followed by the Bonferroni test to check inter-group differences. $p<0.01$; ***$p<0.001$ vs. 0. H), MTT assay to evaluate cell viability/toxicity after treatments. I), Serum-deprived MEFs were subjected to 10 μM of PHAR. The mRNA levels of Hmox1, Nqo1, Aox1, Glc, and Gclm after 8 h of treatment were determined by means of pRT-PCR and normalized by means of average LaminB, Gapdh, and β-actin. The data is depicted as means±SEM (n=3). Statistical analysis was performed with the Student's T test. *$p<0.05$; $p<0.01$ *$p<0.001$ vs. 0.
Figure 4B:
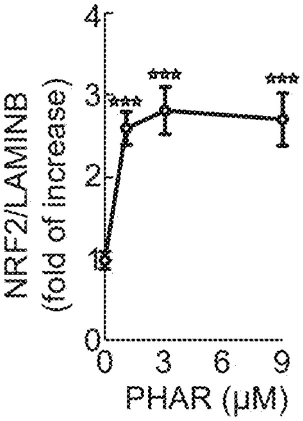
Figure 4C:
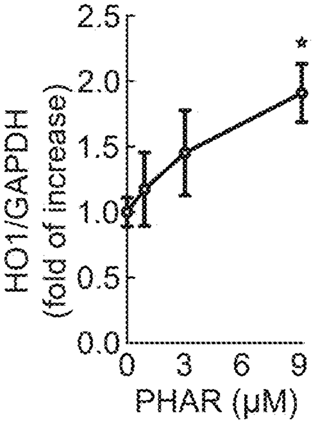

In order to empirically determine if PHAR activates NRF2, mouse embryo fibroblasts (MEFs) were treated with several doses of the compound (1 μM, 3 μM, and 9 μM) for 16 h and with 10 μM of sulforaphane (SFN), one of main electrophilic activators of NRF2, used as a positive control. PHAR induced NRF2 accumulation, although to a slightly lesser extent than the accumulation induced by SFN. This NRF2 accumulation was reflected in an increase, mainly with the dose of 9 μM, in the levels of one of its best characterized targets: heme oxygenase-1 (HO-1) (FIGS. 4A, 4B, and 4C).

Figure 4D:
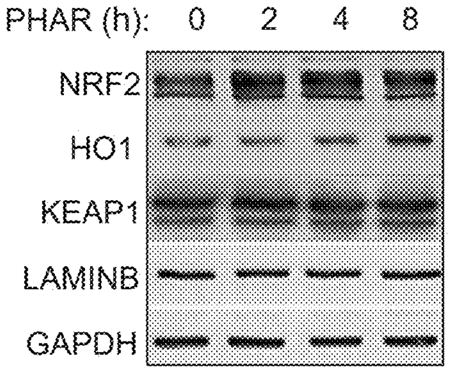
Figure 4E:
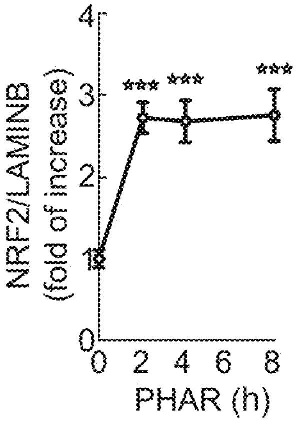
Figure 4F:
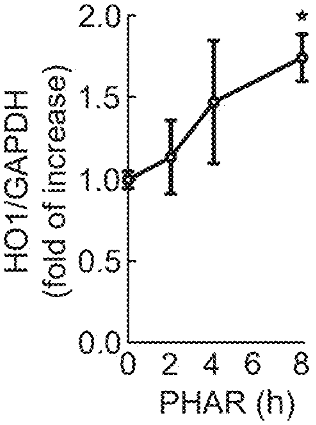

Moreover, a time course of NRF2 activation with PHAR (10 μM for 2, 4, and 8 h) or with SFN (10 μM, 8 h) was done as a positive control. PHAR induced NRF2 accumulation 2 h after treatment which was similar to the induction generated by SFN. Said accumulation correlated with the increase in HO-1 levels after 8 h (FIGS. 4D, 4E, and 4F).

Figure 4G:
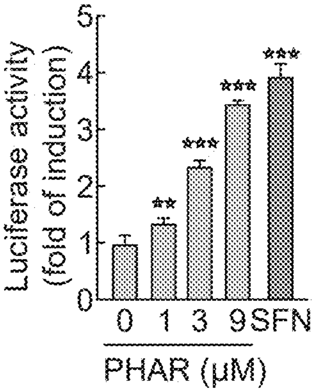
Figure 4H:
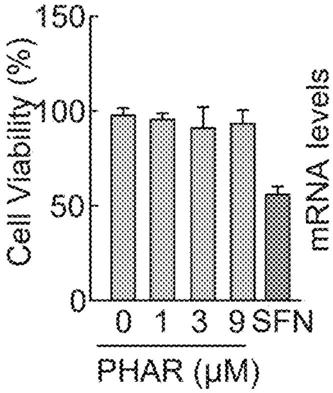
Figure 4I:
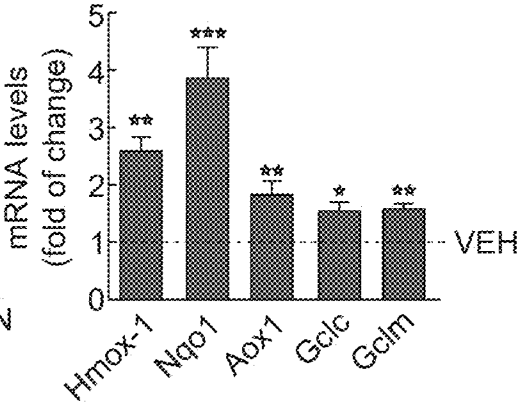

Finally, the transcriptional activity of NRF2 was corroborated by means of luciferase assays using the reporter cell line MCF-7 c32 ARE-LUC. It is observed that PHAR (9 μM, 16 h) produces a ~4-fold increase in luciferase activity, similar to that obtained with the positive control (SFN, 9 μM, 16 h) (FIG. 4G). Cell viability associated with treatment, evaluated by means of an MTT assay, demonstrated that the compound does not present toxicity at any of the doses used (FIG. 4H). Finally, said transcriptional activity was corroborated in MEFs by means of evaluating the expression levels of several NRF2-regulated genes after treatment with PHAR (10 μM, 8 h). The analyzed targets were Hmox1, Nqo1, Aox1, Gclc, and Gclmy an increase in the corresponding transcripts was observed in all the cases (FIG. 4I).

As a whole, these results indicate that PHAR stabilizes NRF2 levels, and as a result increases the expression of its target genes.

Example 1.3. PHAR Activates the NRF2/HO-1 Axis Independently of KEAP1

Figure 5A:
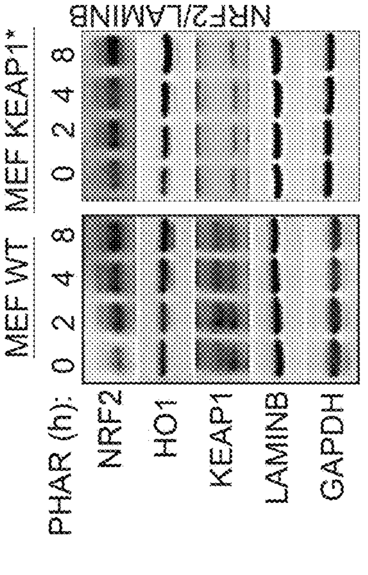
FIG. 5. PHAR-mediated NRF2 activation is independent of KEAP1 and is responsible for the increase in the expression of its targets. (A-D) Serum-deprived MEFs originating from wild-type (WT) or KEAP1 null (Keap1−/−) mice were treated with 10 μM of PHAR for the indicated times. 0.1% DMSO was used as a vehicle. A), representative immunoblots of NRF2, HO1, KEAP1, LAMINB, and GAPDH as loading controls. B) and C), densitometric analysis of NRF2 and HO1 protein levels of the representative immunoblots of (A), expressed as a ratio of NRF2/LAMINB or HO1/GAPDH. The data is depicted as means±SEM (n=3). Statistical analysis was performed with two-way ANOVA followed by the Bonferroni test to check inter-group differences. D), the mRNA levels of Hmox-1, Nqo1, Aox1, Gc1c, and Gc1m were determined after 8 h of 10 μM PHAR by means of qRT-PCR and normalized by means of average Gapdh, Tbp, and β-actin. The data is depicted as mean±SEM (n=3). Statistical analysis was performed with two-way ANOVA followed by the Bonferroni test to check inter-group differences. *$p<0.05$; $p<0.01$; *$p<0.001$ vs. 0 of MEF-WT. (E-H), Serum-deprived MEFs from wild-type (WT) or NRF2 null (Nrf2−/−) mice were subjected to 10 μM of PHAR for the indicated times. 0.1% DMSO was used as a vehicle. E), representative immunoblots of NRF2, HO1, KEAP1, LAMINB, and GAPDH as loading controls. F) and G), densitometric analysis of NRF2 and HO1 protein levels of the representative immunoblots of (E), expressed as a ratio of NRF2/LAMINB or HO1/GAPDH. The data is depicted as means±SEM (n=3). Statistical analysis was performed with two-way ANOVA followed by the Bonferroni test to check inter-group differences. *$p<0.5$; $p<0.01$; p*<0.001 vs. MET WT. H), the mRNA levels of Hmox-1, Nqo1, Aox1, Gclc, and Gclm were determined after 8 h of 10 μM PHAR by means of qRT-PCR and normalized by means of average Gapdh, Tbp, and β-actin. The data is depicted as mean±SEM (n=3). Statistical analysis was performed with two-way ANOVA followed by the Bonferroni test to check inter-group differences. *$p<0.05$; $p<0.01$; *$p<0.001$ vs. MEF-WT.
Figure 5B:
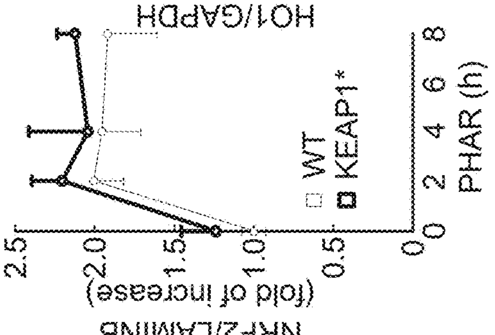
Figure 5C:
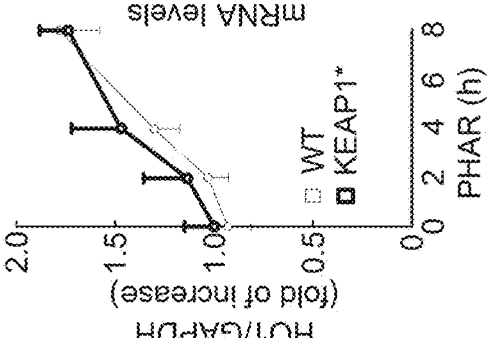
Figure 5D:
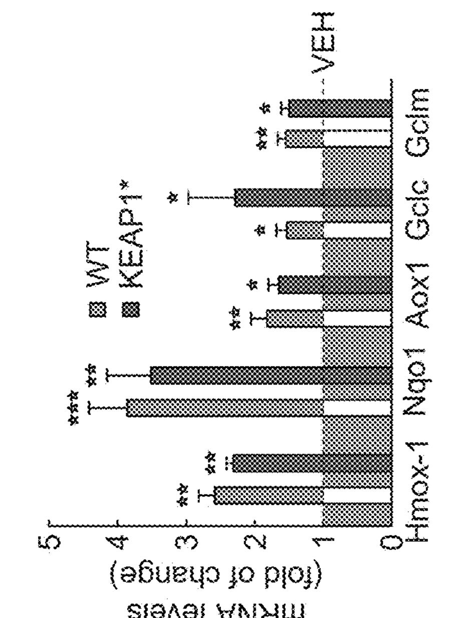
Figure 5E:
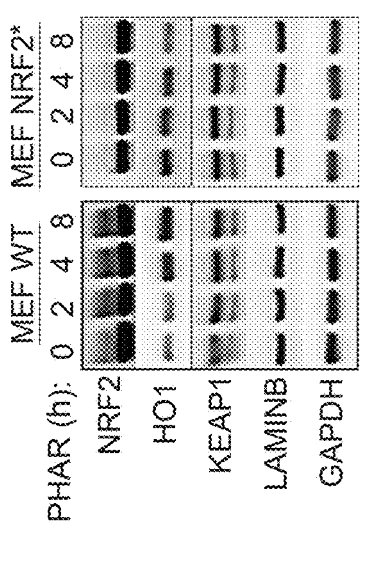
Figure 5F:
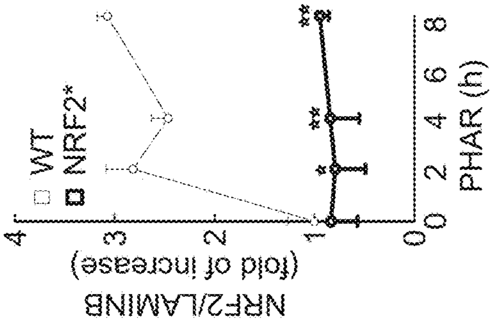
Figure 5G:
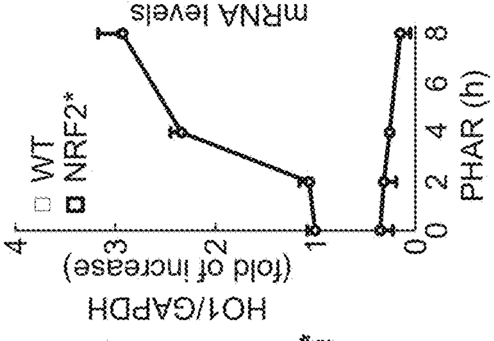
Figure 5H:
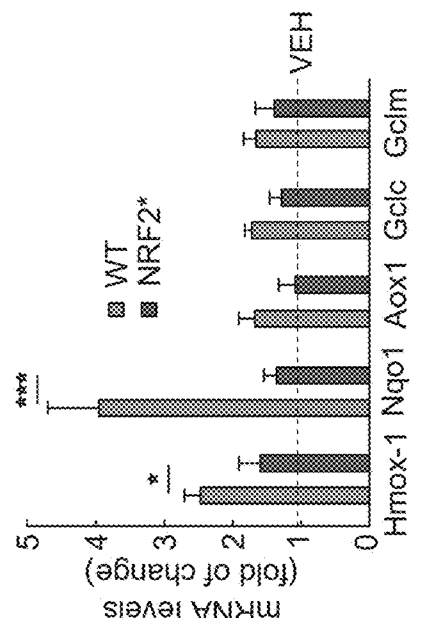

From a viewpoint of biopharmaceutical usefulness, it is important to determine if PHAR acts on KEAP1/NRF2 interaction, or if it represents, in contrast, a novel approach directed specifically at β-TrCP/NRF2 interaction. For this purpose, MEFs originating from KEAP1 knock-out ($Keap1^{-/-}$) and wild type ($Keap1^{+/+}$) mice from the same litter (FIGS. 5A, 5B, 5C, and 5D) were used. NRF2 and HO-1 induction was similar in both cell lines treated with PHAR (10 μM, 2, 4, and 8 h) (FIGS. 5A, 5B, and 5C). The same result was obtained upon analyzing the mRNA levels of other NRF2 targets (FIG. 5D). As an additional control, the HO-1 levels in MEFs originating from NRF2 knock-out ($Nrf2^{-/-}$) and wild-type ($Nrf2^{+/+}$) mice from the same litter were analyzed by immunoblot. Both cell types were incubated with PHAR (10 μM, 2, 4, and 8 h). MEFs originating from $Nrf2^{+/+}$ mice showed a significant increase in HO-1 which was not observed in MEFs originating from $Nrf2^{-/-}$ mice (FIGS. 5E and 5G), indicating that NRF2 is essential for the induction of HO-1 by PHAR. The same result was obtained upon analyzing the mRNA levels of several NRF2 targets in both cell types (FIG. 5H). Therefore, PHAR induces NRF2 independently of KEAP1 and said activation is responsible for the increase in the expression of its target genes.

Example 1.4. PHAR Blocks β-TrCP/NRF2 Interaction

Figures 6A, 6B, 6C, 6D, 6E:
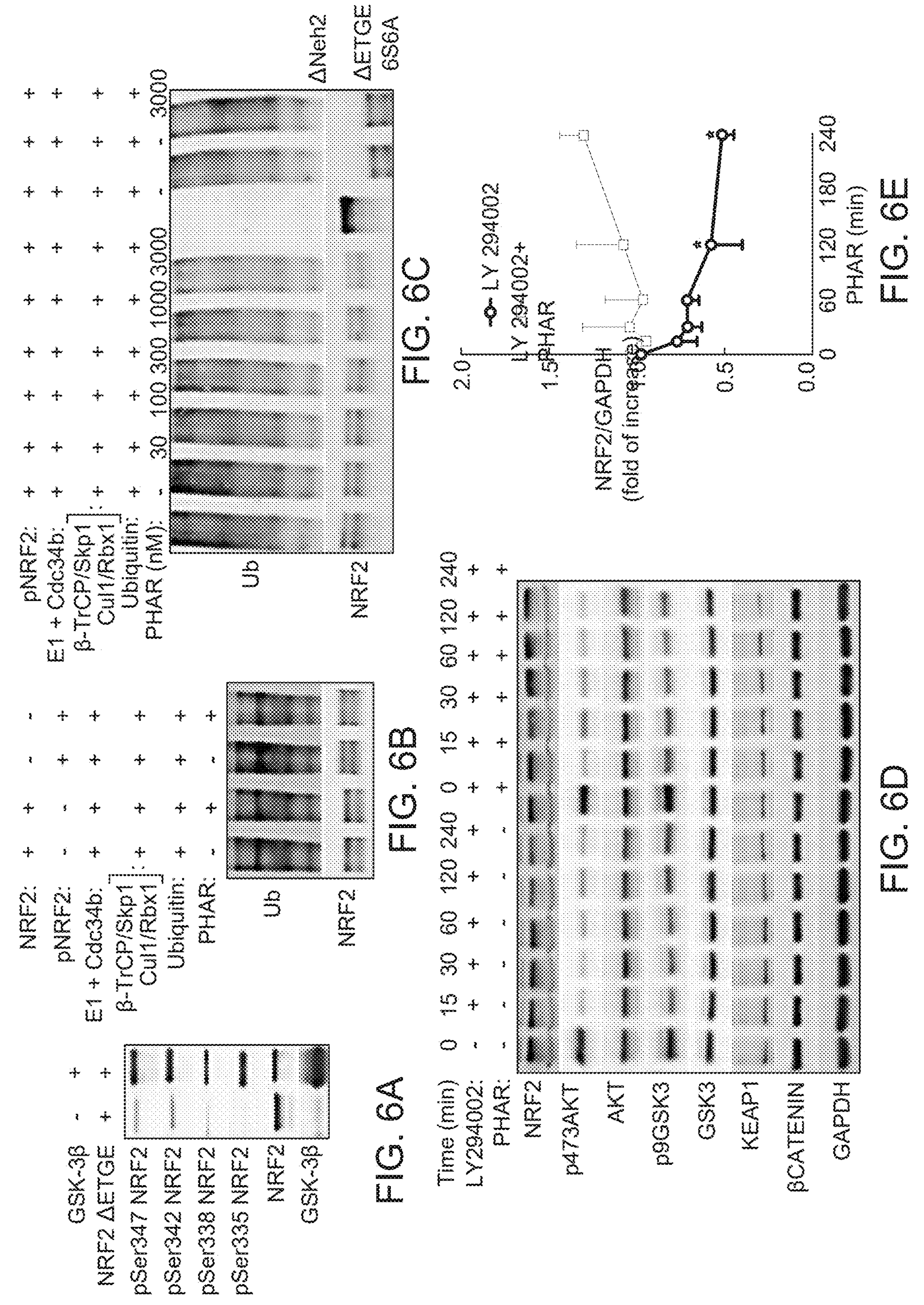
FIG. 6. PHAR increases NRF2 protein levels in a β-TrCP-dependent manner. A) In vitro phosphorylation of recombinant NRF2-DETGE by recombinant GSK-3β. Phosphorylation at residues 335, 338, 342 and 347 was analyzed by western blot. B) In vitro ubiquitination of NRF2 or pNRF2 by the βTrCP complex. NRF2 and pNRF2 (20 ng) were incubated at 25° C. for 1 h with purified ubiquitin, E1/cdc34b, βTrCP/Skp1 and Cull/Rbx1 as indicated in the presence or absence of PHAR (3 mM) or vehicle (DMSO). Polyubiquitinated NRF2 was detected by western blot with anti-ubiquitin antibody. C) under the same conditions detailed in B) a PHAR dose curve (3-3000 nM) was carried out to fix the minimum dose in which PHAR prevents the poly-ubiquitination of NRF2. Recombinant NRF2-DETGE-6S6A, in which the 6 serines capable of being phosphorylated for the Neh6 domain have been mutated to alanines, was used as a negative control. (D) and E) Serum-deprived MEFs from KEAP1 null mice ($Keap1^{-/-}$) were treated with 10 μM of PHAR for 60 min. 0.1% DMSO was used as a vehicle. The cells were then treated with 20 μM of LY294002 for the indicated times. D), representative immunoblots of NRF2, pSer473-AKT, AKT, pS9-GSK3, GSK3, KEAP1, and GAPDH as loading controls. E), densitometric analysis of NRF2 protein levels of the representative immunoblot of (D), expressed as a ratio of NRF2/GAPDH. The data is depicted as means±SEM (n=3). Statistical analysis was performed with two-way ANOVA followed by the Bonferroni test to compare inter-group differences. *$p<0.05$ vs. LY294002. MEF originating from $Keap1^{-/-}$ mice were transduced with a lentivirus encoding mouse shCTRL or anti-p-TrCP1/2 sh. The serum-deprived MEFs were subjected to 10 μM of PHAR for the indicated times. 0.1% DMSO was used as a vehicle. F), representative immunoblots of NRF2, β-CATENIN, HO1, KEAP1, and GAPDH as loading controls. G), densitometric analysis of NRF2 and HO1 protein levels of the representative immunoblots of (F), expressed as a ratio of NRF2 and HO1/GAPDH. The data is depicted as means±SEM (n=3). Statistical analysis was performed with two-way ANOVA followed by the Bonferroni test to check inter-group differences. $p<0.01$; *$p<0.001$ vs. shCTRL. H) and I), the mRNA levels of p-TrCP1, β-TrCP2, Hmox-1, and Nqo1 were determined by means of qRT-PCR and normalized by means of average Gapdh, Tbp, and β-actin. The data is depicted as mean±SEM (n=3). Statistical analysis was performed with two-way ANOVA followed by the Bonferroni test to check inter-group differences. ***$p<0.001$ vs. shCTRL.

In silico studies suggested that PHAR increases NRF2 levels by means of inhibiting NRF2-β-TrCP interaction. To confirm this, first, we performed an in vitro ubiquitination assay to see if PHAR prevents the ubiquitination of NRF2 by βTrCP. For βTrCP to be able to recognize and degrade NRF2, NRF2 must be labelled first by phosphorylation at serines 335, 337, 342 and 347, located in the Neh6 domain, that are carried out, at least in part, by GSK-3β. In order to get the phosphorylated NRF2, we performed an in vitro GSK-3β kinase assay with recombinant NRF2-DETGE, for 1 h at 25° C. Western blot analysis revealed that the described serines were adequately phosphorylated (FIG. 6A). Next, both the phosphorylated and non-phosphorylated substrates were subjected to in vitro ubiquitination asssay in the presence and absence of PHAR. As shown in FIG. 6B, the substrate was polyubiquitinated to a greater extent when it was previously phosphorylated. Interestingly, this polyubiquitination was considerably lower when the PH was present. Next, we performed a dose curve with the same procedure (FIG. 6C) and PHAR starts to reduce substrate polyubiquitination from the 100 nM concentration.

The next approach was to inhibit the PI3K/AKT signaling pathway, leading to GSK-3β activation, with the PI3K inhibitor, LY294002. As a result, NRF2 is phosphorylated in its Neh6 domain and marked for degradation by means of interaction with β-TrCP. Therefore, if PHAR inhibits β-TrCP-NRF2 interaction, according to in silico predictions, NRF2 levels will remain stable independently of the activation and phosphorylation by GSK-3β. Furthermore, to once again rule out a possible KEAP1-mediated alternative mechanism, MEFs originating from $Keap1^{-/-}$ mice were used. These cells were pretreated with 10 μM of PHAR or DMSO as a vehicle for 1 h and treatment with LY294002 (20 μM, 15, 30, 60, 120, and 240 min) was then carried out. LY294002 caused a reduction of pSer473-AKT (by inactivating it) and pS9-GSK3 (by activating it) (FIG. 6D), and furthermore caused a drop in NRF2 levels which can be observed mainly after 120 and 240 min of treatment. In contrast, pre-treatment with PHAR not only prevented LY294002-induced NRF2 degradation, but furthermore favored NRF2 accumulation independently of the activation of GSK3-β/β-TrCP (FIGS. 6D and 6E). Therefore, these results suggest that PHAR promotes NRF2 accumulation by means of inhibiting interaction with β-TrCP.

Figure 6F:
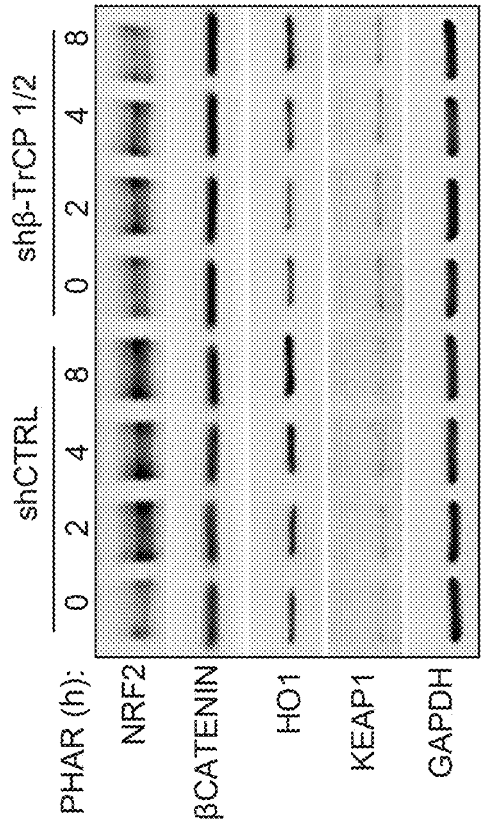
Figure 6G:
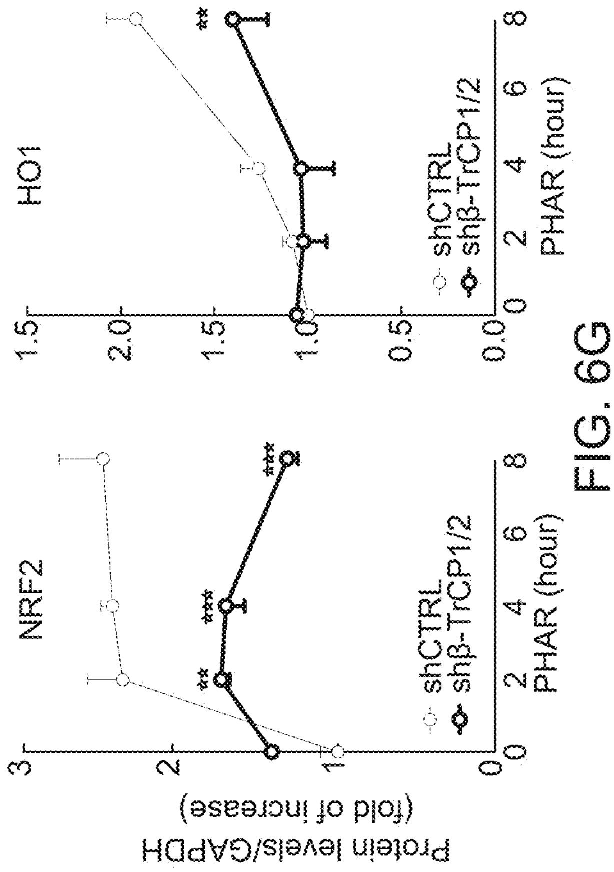
Figure 6H:
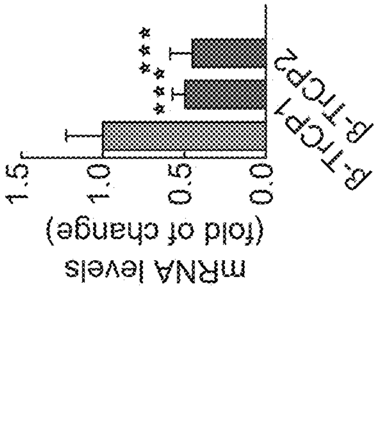
Figure 6I:
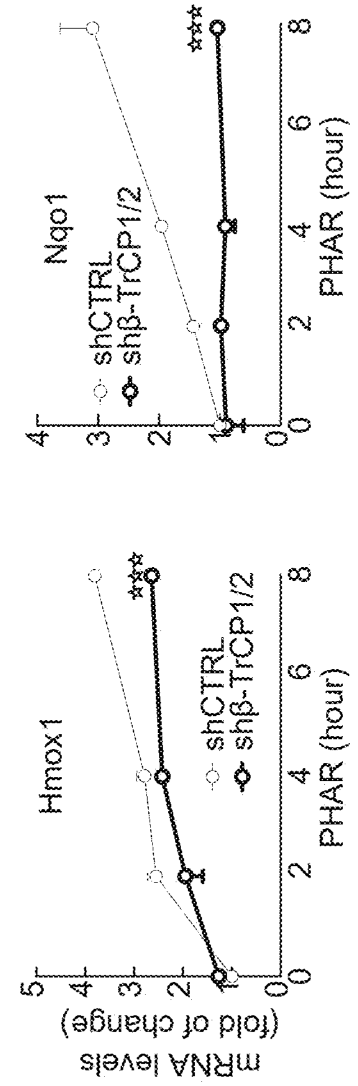

In other experiments, silencing of the two isoforms described for β-TrCP (β-TrCP1 and β-TrCP2) was performed in MEFs originating from $Keap1^{-/-}$ mice. Silencing was performed by means of infection with lentiviral vectors shRNA control (shCTRL) or β-TrCP1 and β-TrCP2 (sh β-TrCP1/2) for 5 days followed by selection of the infected cells with puromycin. Once silencing was performed, the cells were treated with PHAR (10 μM, 2, 4, and 8 h). Although the silencing achieved was about 50% for both isoforms (FIG. 6H), this was sufficient to observe a significant increase in levels of β-catenin protein, used as the β-TrCP silencing control as it is one of its main targets (FIG. 6F). In these conditions, it can be seen in shCTRL cells that PHAR causes an increase in NRF2 levels from 2 h to 8 h after sustained treatment. In contrast, the partial silencing of β-TrCP1/2 caused a slight increase in baseline NRF2 levels compared with shCTRL. However, although NRF2 accumulation occurred as a result of the treatment (probably due to the silencing achieved not being 100%), this accumulation was significantly lower compared with shCTRL cells (FIGS. 6F and 6G). Likewise, HO-1 accumulation was lower in cells lacking β-TrCP1/2 (FIGS. 6F and 6G). The mRNA levels corresponding to conventional NRF2 targets, Hmox1 and Nqo1, confirmed the result obtained in protein, seeing that the induction generated by PHAR is lost with the silencing of both isoforms of β-TrCP (FIG. 6I). Therefore, it can be concluded that the mechanism of action of the PHAR compound is mediated by its capacity to inhibit β-TrCP-NRF2 interaction.

Example 1.5. PHAR Reduces Inflammatory Response in LPS-Stimulated Cells

Once the mechanism of action of PHAR was deciphered, the capacity thereof to carry out protection against general lipopolysaccharide (LPS)-induced inflammation was evaluated. The NRF2/HO-1 axis contributes to inflammation resolution through direct and indirect mechanisms. Direct mechanisms include transcriptional induction of anti-inflammatory genes (MARCO, CD36), as well as transcriptional repression of pro-inflammatory genes (IL6, IL1β). Indirect mechanisms involve the inhibition of reactive oxygen species and reactive nitrogen species (ROS/RNS) or of the migration/infiltration of immune cells. Furthermore, the NRF2-ARE pathway is in equilibrium with the NF-κB pro-inflammatory pathway.

Figures 7A, 7B, 7C, 7E:
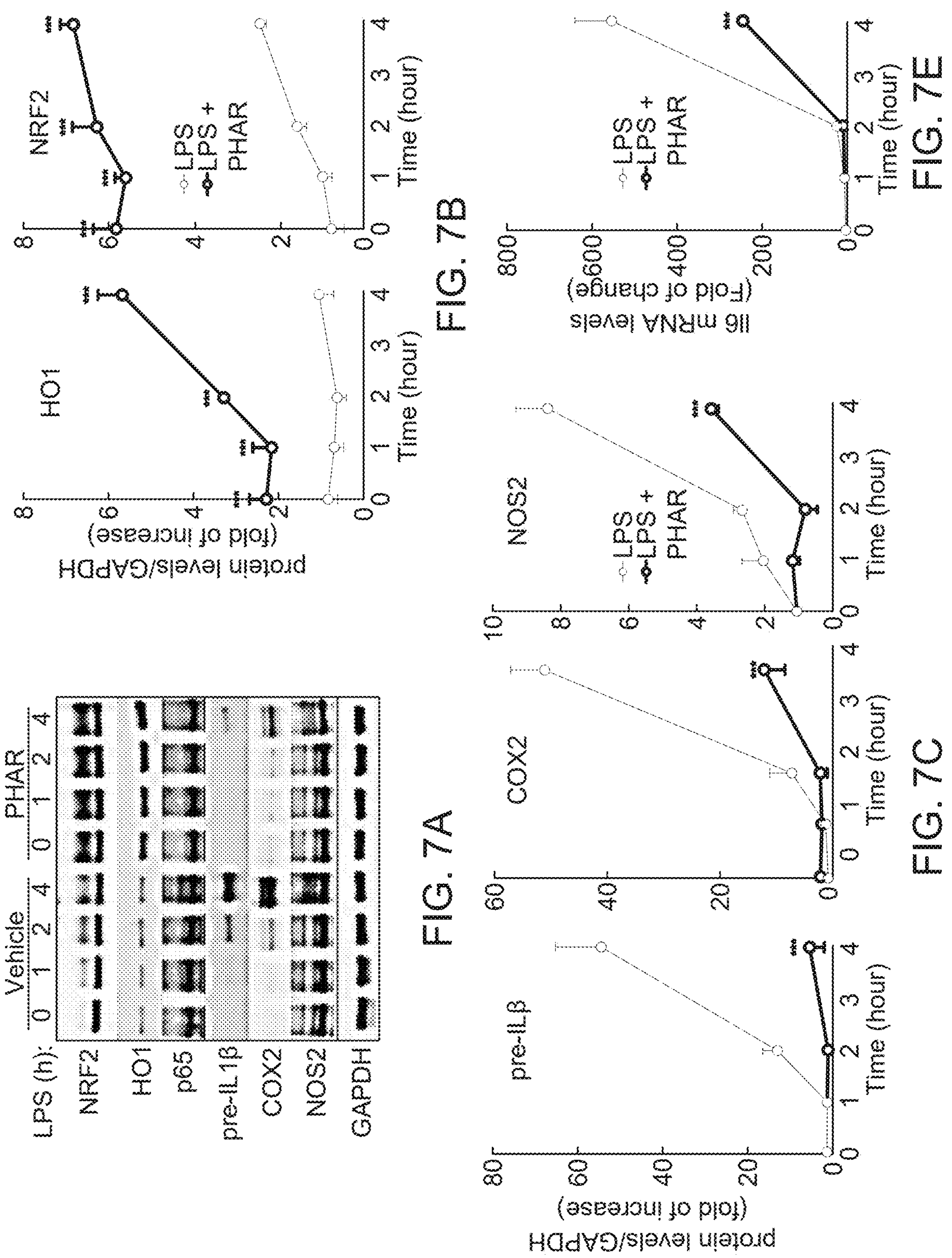
FIG. 7. PHAR reduces inflammatory response in LPS-stimulated Raw264.7 cells. Serum-deprived Raw264.7 cells were pretreated with 10 μM of PHAR for 8 h. 0.1% DMSO was used as a vehicle. After that period of time, the cells were treated with 100 ng/ml of LPS for the indicated times. A), representative immunoblots of NRF2, HO1, p65, pre-IL1β, COX2, NOS2, and GAPDH as a loading control. The black arrow tip marks the specific band of p65 and NOS2. B), densitometric analysis of HO1 and NRF2 protein levels of the representative immunoblots of (A), expressed as a ratio of protein/GAPDH levels. The data is depicted as means±SEM (n=3). Statistical analysis was performed with two-way ANOVA followed by the Bonferroni test to compare inter-group differences. *p<0.001 vs LPS. C), Densitometric analysis of pre-IL1β, COX2, and NOS2 protein levels of the representative immunoblots of (A), expressed as a ratio of protein/GAPDH levels. The data is depicted as means±SEM (n=3). Statistical analysis was performed with two-way ANOVA followed by the Bonferroni test to compare inter-group differences. *p<0.001 vs. LPS. D) and E), the mRNA levels of Il1β, Cox2, Nos2, Il6, and Tnfα were determined by means of qRT-PCR and normalized by means of average Gapdh, Tbp, and β-actin. The data is depicted as mean±SEM (n=3). Statistical analysis was performed with two-way ANOVA followed by the Bonferroni test to check inter-group differences. ***p<0.001 vs. LPS.
Figure 7D:
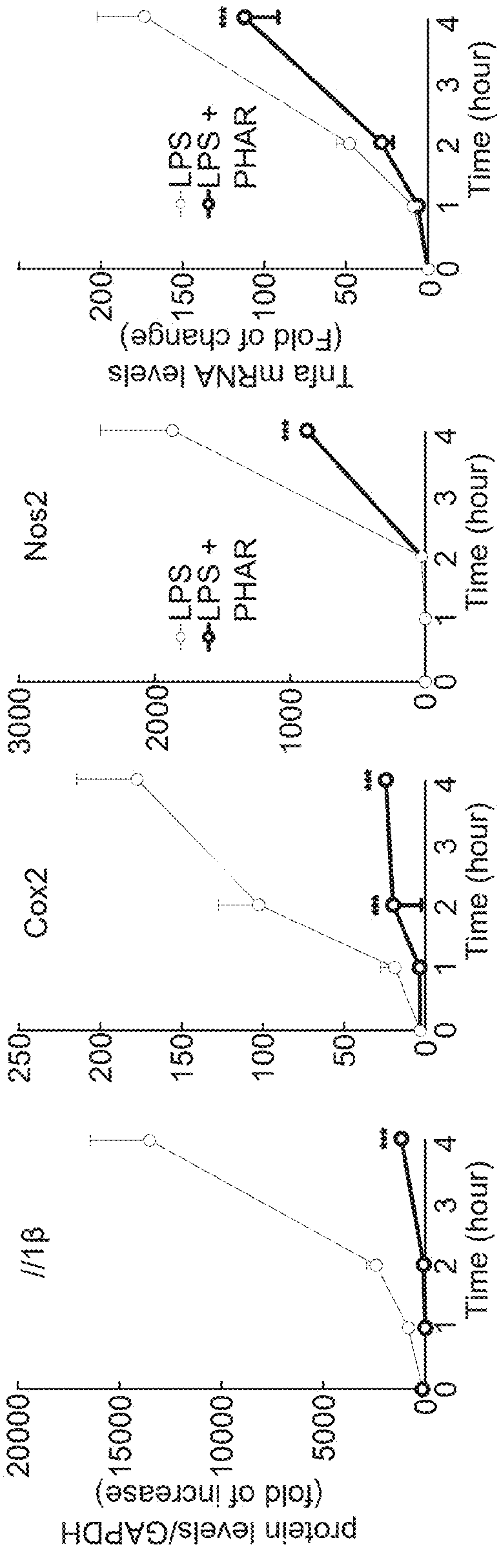

First, an established mouse macrophage cell line (Raw264.7) is used and subjected to pre-treatment with a vehicle (DMSO) or PHAR (10 μM, 8 h) to obtain increased NRF2 and HO-1 levels. The cells were then stimulated with LPS (100 ng/ml, 1, 2, or 4 h) to trigger an inflammatory response. After 4 h of treatment, the LPS indeed caused an increase of several inflammatory markers: p65, pre-IL1β, NOS2, and COX2 (FIGS. 7A and 7C). In contrast, pretreatment with PHAR increased NRF2 and HO-1 levels (FIGS. 7A and 7B) but, furthermore, mitigated the increase in inflammatory parameters determined by immunoblot (FIGS. 7A and 7C) or by mRNA levels (Il1β, Cox2, Nos2) (FIG. 7D). Furthermore, other pro-inflammatory cytokines (Il6 and Tnfa) also experienced a significantly milder induction in cells pretreated with PHAR (FIG. 7E). Therefore, PHAR reduces the inflammatory response in response to LPS in Raw264.7 cells.

Figure 8B:
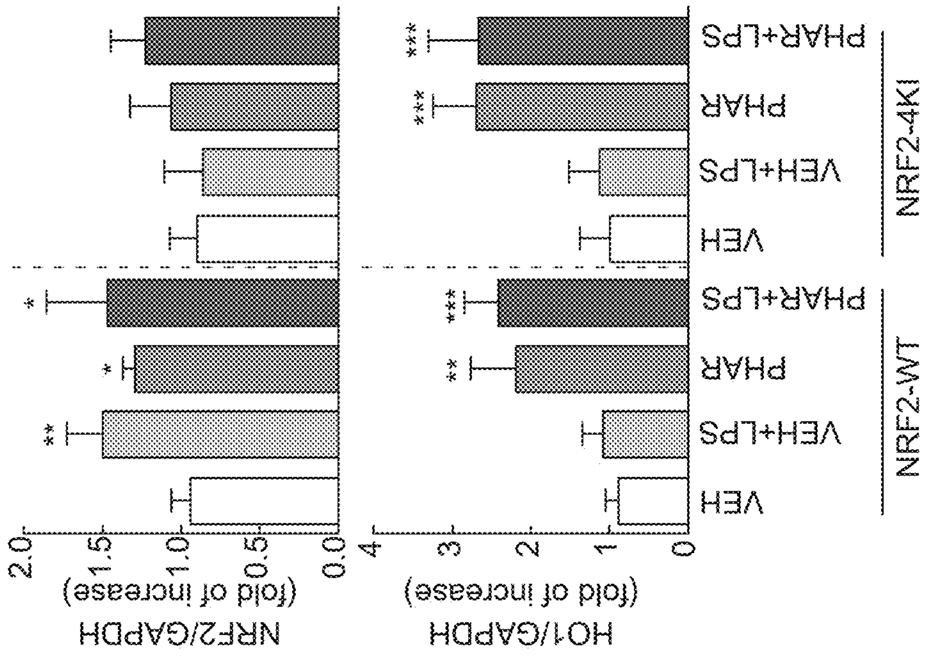
FIG. 8. PHAR reduces inflammatory response in peritoneal macrophages originating from $Nrf2^{+/+}$ mice but not in peritoneal macrophages originating from LPS-stimulated Nrf2-4KI mice. Peritoneal macrophages originating from wild-type (WT) and serum-deprived NRF2 knock-in (Nrf2-4Ki) mice were pretreated with 10 μM of PHAR for 8 h. 0.1% DMSO was used as a vehicle. After that period of time, the cells were treated with 100 ng/ml of LPS for 4 h. A), representative immunoblots originating from both cell types of NRF2, HO1, pre-IL1β, COX2, NOS2, and GAPDH as a loading control. B), densitometric analysis of NRF2 and HO1 protein levels of the representative immunoblots of (A), expressed as a ratio of protein/GAPDH levels. The data is depicted as means±SEM (n=3). Statistical analysis was performed with two-way ANOVA followed by the Bonferroni test to compare inter-group differences. *p<0.05; p<0.01; *p<0.001 vs. LPS. C), Densitometric analysis of pre-IL1b, COX2, and NOS2 protein levels of the representative immunoblots of (A), expressed as a ratio of protein/GAPDH levels. The data is depicted as means±SEM (n=3). Statistical analysis was performed with two-way ANOVA followed by the Bonferroni test to compare inter-group differences. *p<0.05; p<0.01; *p<0.001 vs. LPS. D), the mRNA levels of Hmox1, Il1 β, Cox2, Nos2, Il6, and Tnfα were determined by means of qRT-PCR and normalized by means of average Gapdh, Thp, and β-actin. The data is depicted as mean±SEM (n=3). Statistical analysis was performed with two-way ANOVA followed by the Bonferroni test to check inter-group differences. *p<0.05; p<0.01; *p<0.001 vs. LPS.
Figure 8A:
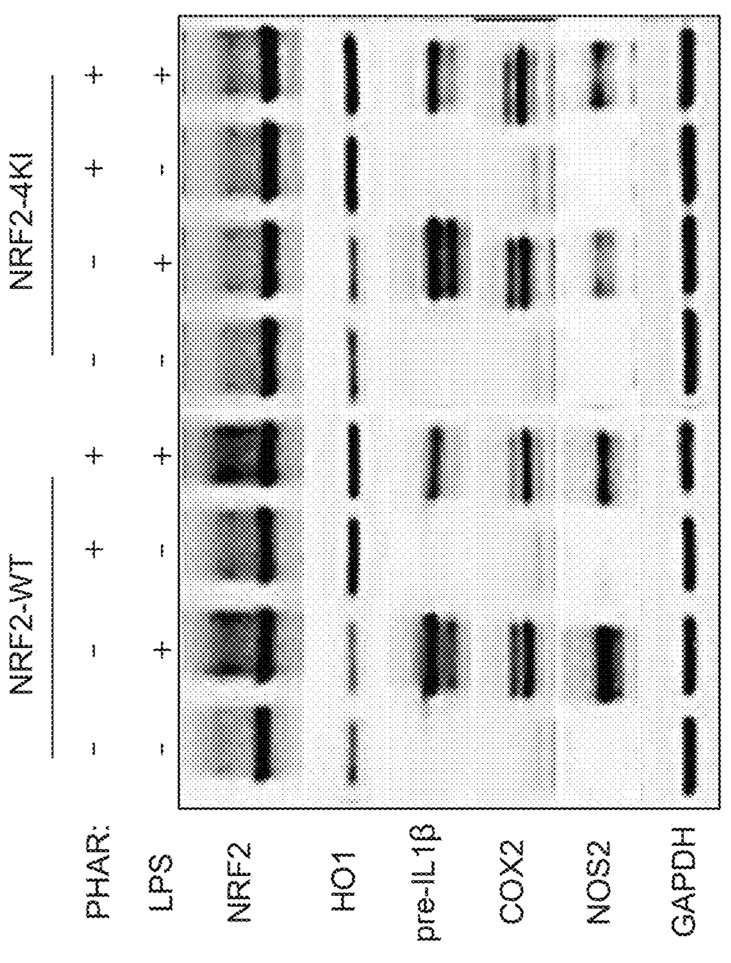
Figure 8C:
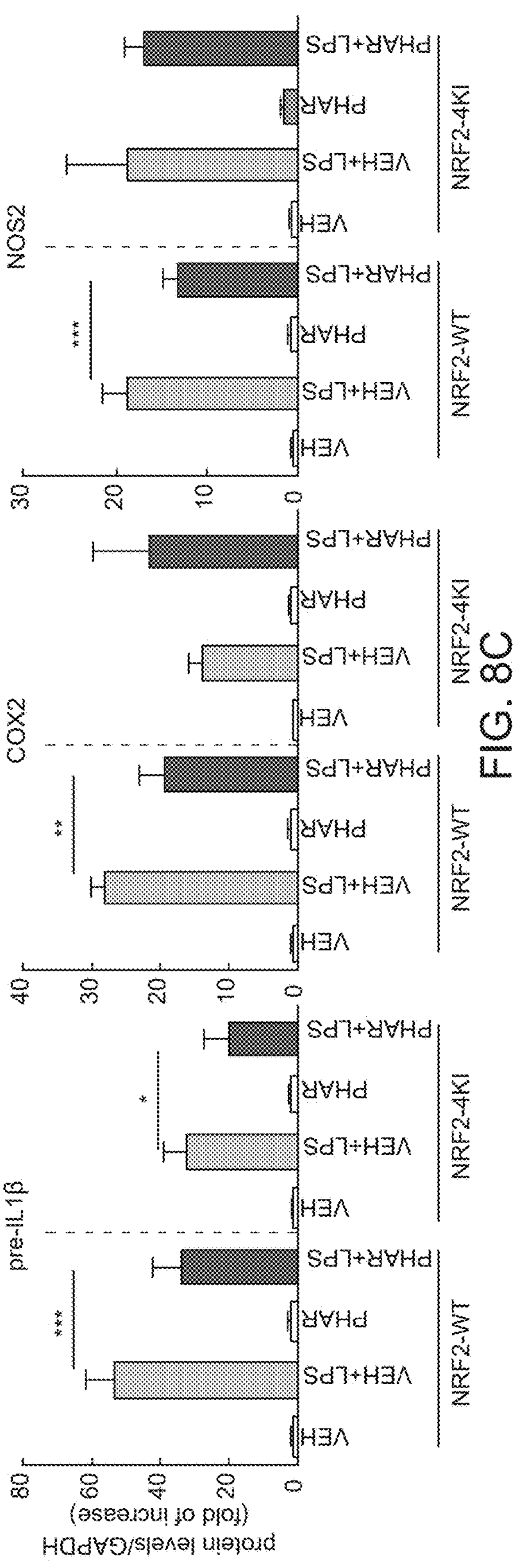
Figure 8D:
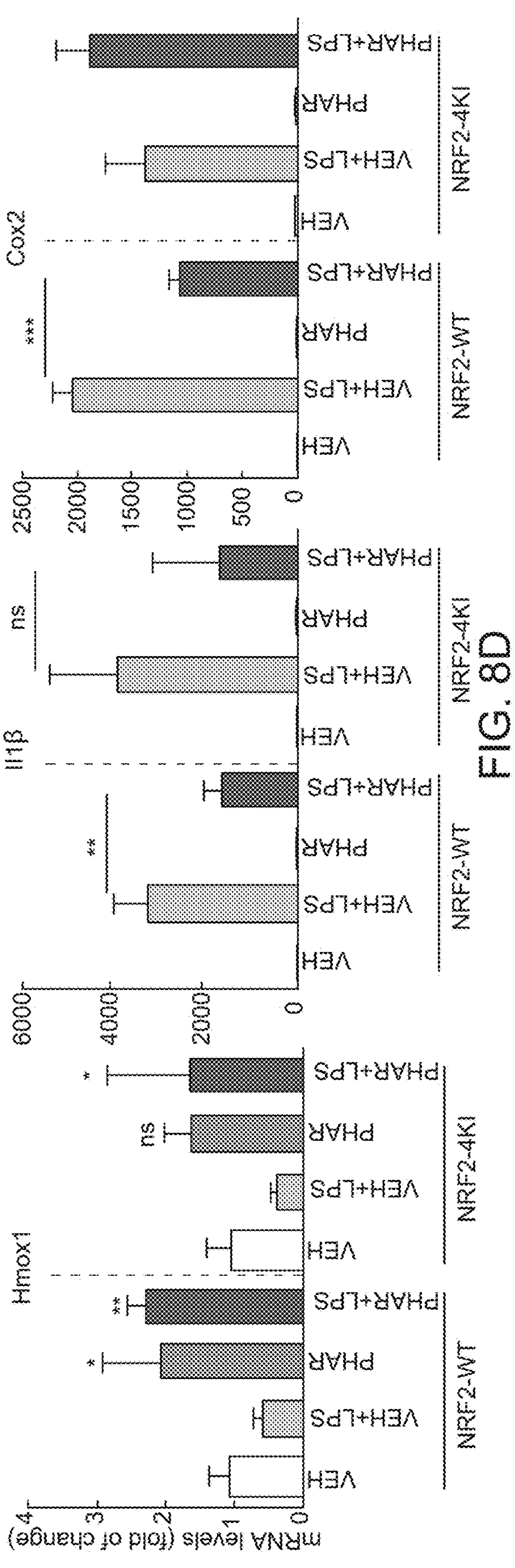
Figure 8D:
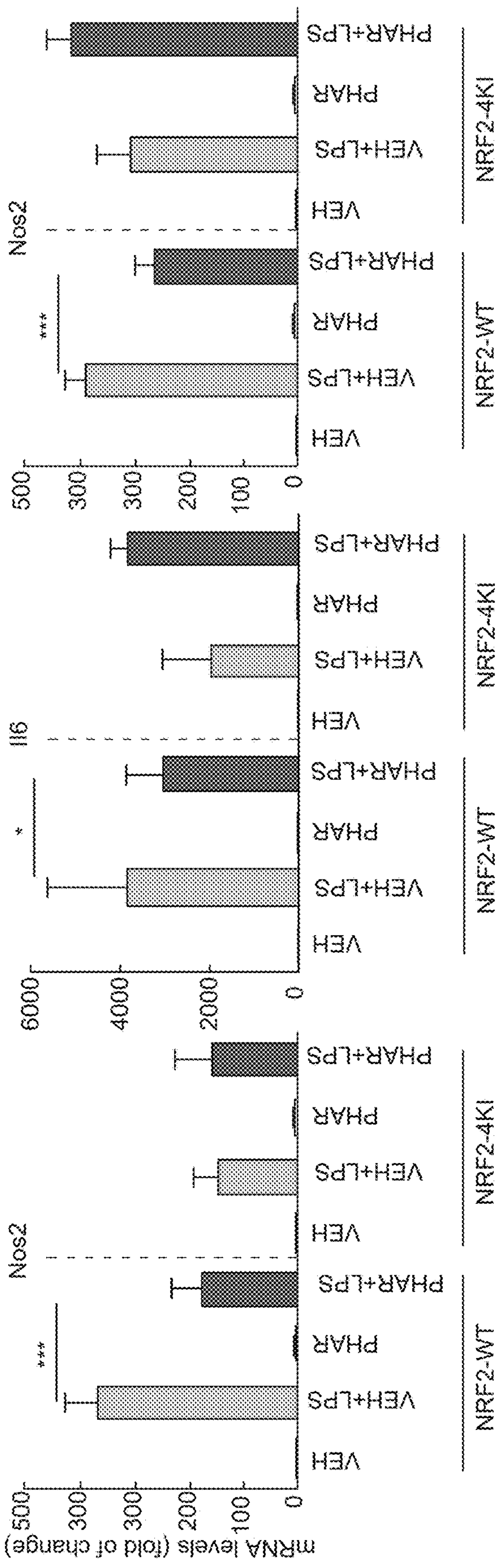

As a complementary approach, peritoneal macrophages extracted from $Nrf2^{+/+}$ mice and knock-in mice generated in the laboratory having 4 serines substituted with alanines in critical positions for phosphorylation by priming kinase/priming kinases and by GSK-3β (Serines 335, 338, 342, and 347) were used. Both cell types were pretreated with DMSO or PHAR (10 μM, 8 h) and then stimulated with LPS (100 ng/ml, 4 h). In these cell models, LPS caused an increase in inflammatory markers in peritoneal macrophages originating from $Nrf2^{+/+}$ mice (FIG. 8A left panel and FIG. 8C). Pretreatment with PHAR caused a significant increase in NRF2 and HO-1 protein levels (FIG. 8A left panel and FIG. 8B) but the production of inflammatory markers was significantly lower in those analyzed at the protein level (pre-IL1β, COX2, and NOS2) (FIG. 8A left panel and FIG. 8C) and mRNA level (Il1β, Cox2, Nos2, Il6, and Tnfα) (FIG. 8D). In peritoneal macrophages derived from 4KI (Nrf2-4KI) mice, NRF2 induction in response to PHAR was considerably lower. In contrast, the same HO-1 induction in response to treatment was obtained (FIG. 8A right panel, and FIG. 8B). Interestingly, the protective effect against the PHAR-mediated inflammatory response was lost in almost all the inflammatory markers analyzed both in protein (FIG. 8A right panel and FIG. 8C) in mRNA (FIG. 8D). Therefore, considering all the results as a whole, it can be concluded that PHAR is an anti-inflammatory compound whose mechanism of action is the activation of NRF2 by interrupting the interaction thereof with β-TrCP.

Example 1.6. PHAR Increases Liver NRF2 Protein Levels

Figure 9A:
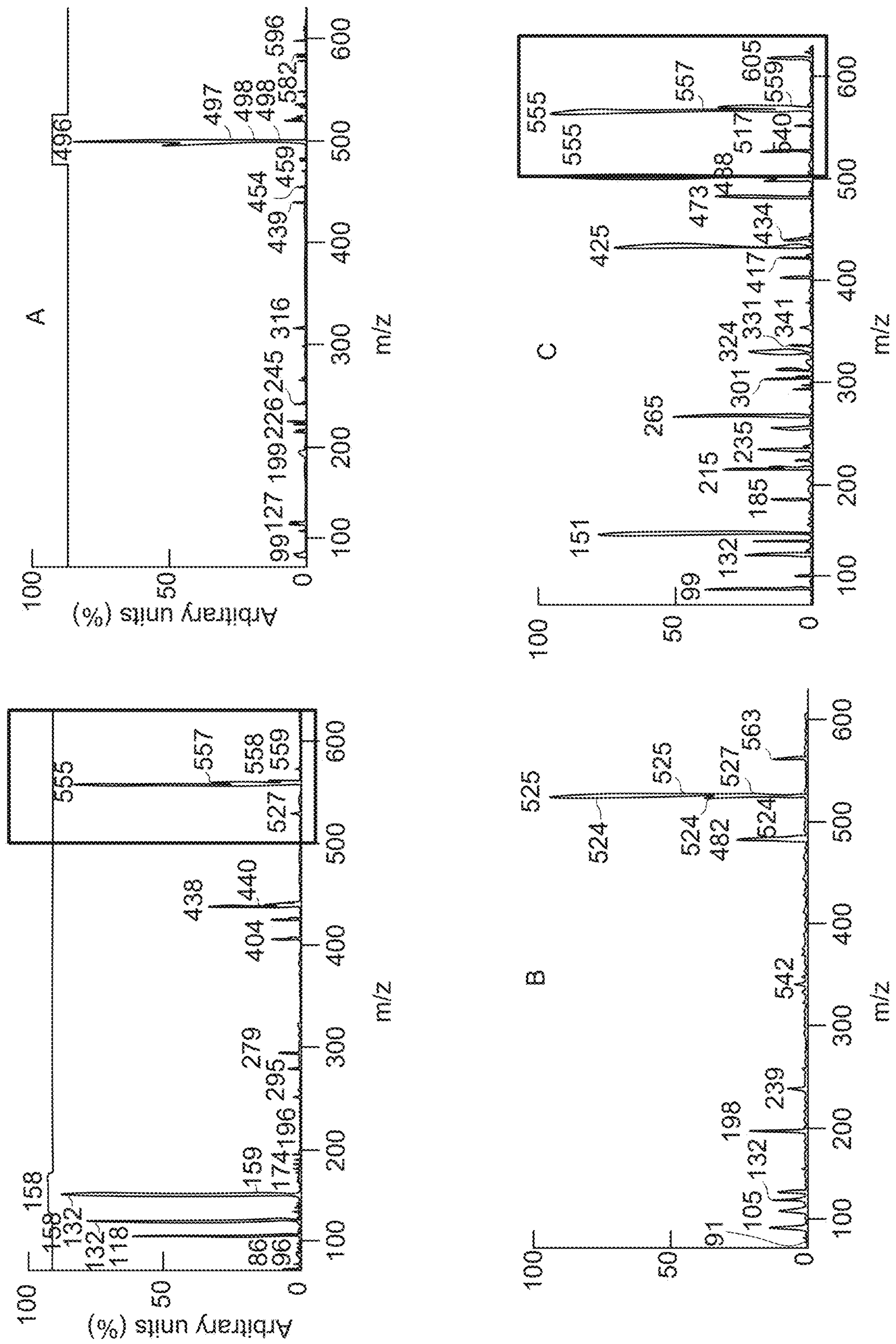
FIG. 9. PHAR activates NRF2 and HO-1 in liver. A), UV and MS spectrum derived from the HPLC-MS analysis of PHAR dissolved in methanol for the identification of peaks associated with the compound. A blue rectangle surrounds the mass associated with PHAR. (B-D), the mice were treated with the vehicle (Tween-80+PBS, 1:13), 50 mg/kg of PHAR, or 50 mg/kg of SFN (saline) as a positive control by means of intraperitoneal (IP) injection for 2 hours. B), HPLC-MS UV and MS spectra derived from representative liver samples of both experimental groups used for determining PHAR levels in the liver 120 min after a single IP injection of 50 mg/kg. A blue rectangle surrounds the mass associated with PHAR. C), representative immunoblots showing NRF2, HO1, and LAMINB protein levels as the liver extract loading control. D), densitometric analysis of NRF2 protein levels of the representative immunoblots shown in (C), expressed as a ratio of NRF2/LAMINB. Statistical analysis was performed with one-way ANOVA followed by the Bonferroni test to compare inter-group differences. *p<0.001 vs. vehicle. E) and F), the mice were treated daily with vehicle (Tween-80+PBS, 1:13) or 50 mg/kg of PHAR by means of intraperitoneal injection for 5 days. E), representative immunoblots showing NRF2, HO1, and LAMINB protein levels as loading control in brain, liver and kidney. F), densitometric analysis of NRF2 and HO1 protein levels in the liver tissue of the representative immunoblots shown in (E), expressed as a ratio of NRF2/LAMINB or HO1/LAMINB levels. Statistical analysis was performed with a Student t test to compare inter-group differences. p<0.01 vs. vehicle.
Figure 9B:
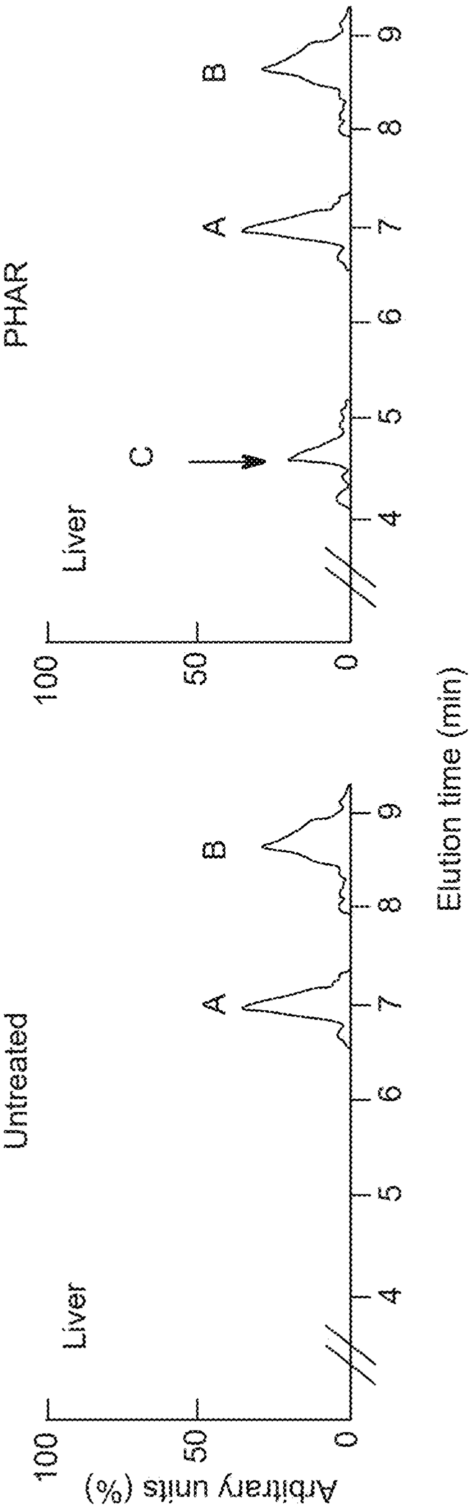
Figure 9D:
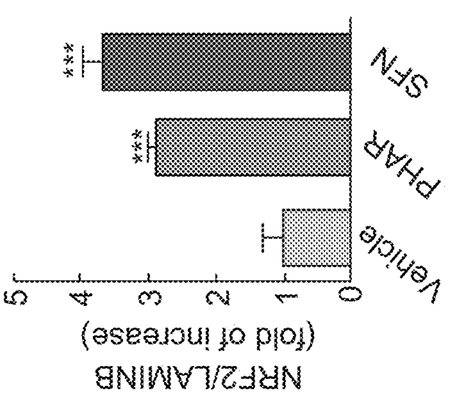
Figure 9C:
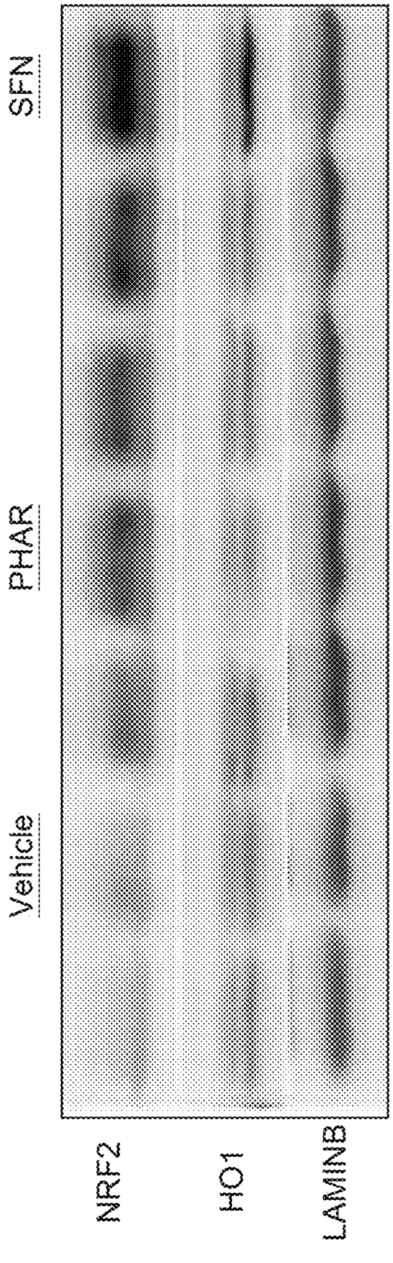

Once the mechanism of action of PHAR was deciphered, the capacity thereof to induce NRF2 levels in a murine model was evaluated. C57BL/6 mice received a single intraperitoneal (IP) injection of 50 mg/kg PHAR (Tween-80+PBS, 1:13) or 50 mg/kg of SFN (saline) as a positive control. The UV spectrum derived from the HPLC-MS study of the PHAR compound dissolved in methanol alone helped the identification of the peak associated with the compound for subsequent identification in the tissue analysis. As shown in FIG. 9A, the PHAR UV spectrum resulted in a peak at about 6 minutes of elution with an associated mass of 555 g/mol, as expected. Taking this as a reference point, liver tissue analysis was performed to check for the presence of PHAR therein. In FIG. 9B, the untreated mice showed two non-specific peaks at about 7 and 9 minutes of elution (referred to in FIG. 9B with letters A and B) identified by means of UV absorbance. However, PHAR-treated mice further showed a new peak at ~4 minutes of elution (letter C). This new peak in treated mice corresponded with the presence of the compound since the mass analysis showed the existence of a mass with a value of 555 g/mol identical to the mass obtained in FIG. 9A. Likewise, analysis of liver NRF2 levels showed significant NRF2 accumulation 120 min after the administration of PHAR which was very similar to the accumulation caused by SFN (FIGS. 9C and 9D). However, this accumulation did not result in increased HO-1 levels, presumably because the duration of treatment was too short to generate an accumulation thereof.

Figure 9E:
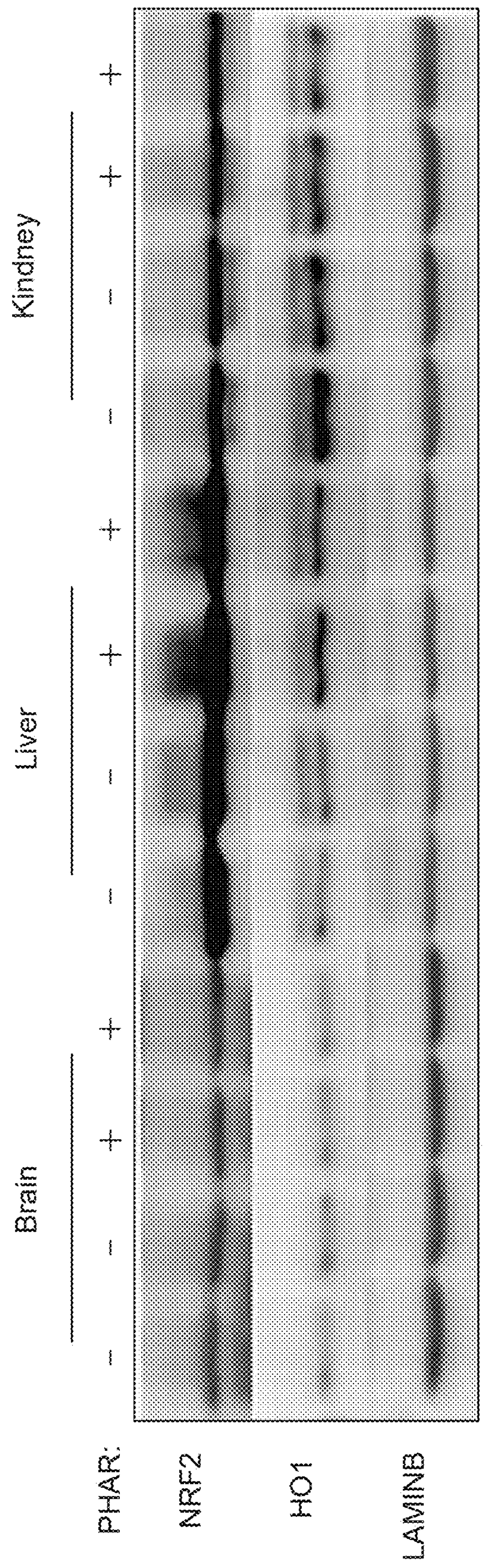
Figure 9F:
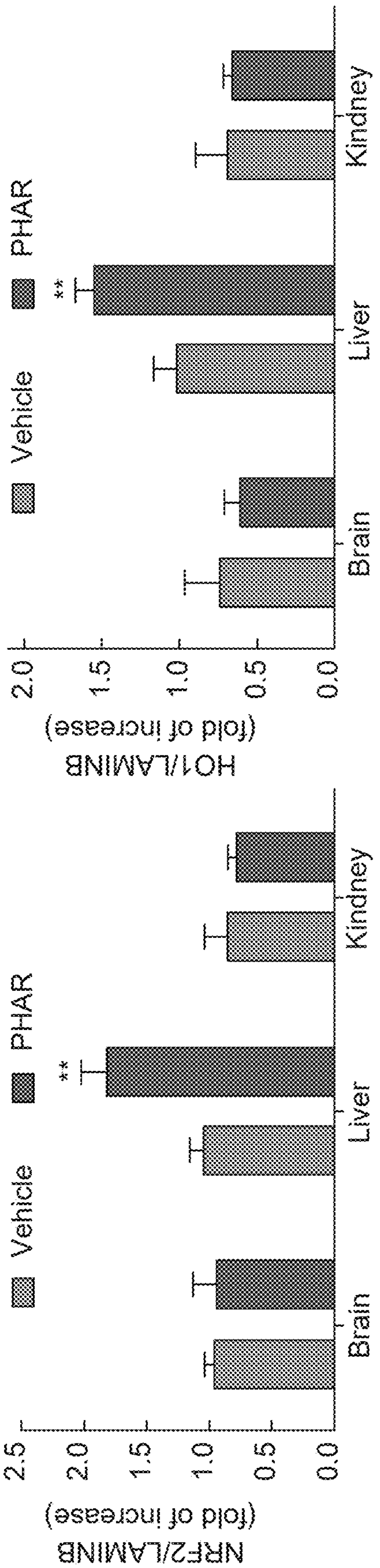

For this reason, C57BL/6 mice were treated daily by IP route for 5 days with 50 mg/kg of vehicle or 50 mg/kg of PHAR. A significant increase of NRF2 and HO-1 in liver (FIGS. 9E and 9F) was observed 120 minutes after the last administration of the compound. By contrast, the levels of NRF2 and HO1 in brain were not modified, In kidney the basal HO1 levels were higher than in liver, but they were not further increased by PHAR. These results indicate that the invention claimed with formula II is active in liver but does not discard that specific molecules included in formula I might also have a therapeutic value in other organs in case of a different pharmacodynamics.

Example 1.7. Prolonged Administration of PHAR in Mice is Safe

Figure 10A:
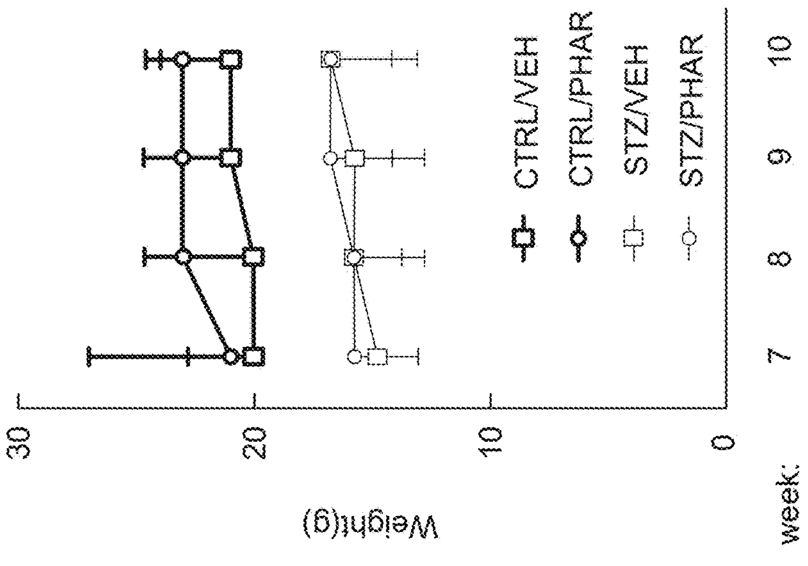
FIG. 10. Chronic PHAR treatment in mice does not produce toxicity. A preliminary safety profile of PHAR treatment was assessed in 7-10 months old control and streptozotocin (STZ) treated mice. These mice were subjected to a daily IP dose of 40 mg/kg of vehicle (VEH; Tween-80:PBS, 1:13), or PHAR for 5 days a week for 4 weeks. A) weight evolution during the weeks of treatment. (B-E) serum analysis of the levels of albumin (B), total protein (C) and liver transaminases, aspartate transaminase, AST (D), and alanine transaminase, ALT (E). The ranges of normal values are highlighted with a green dashed line. The number of individuals per group is reflected in the graphs.
Figure 10B:
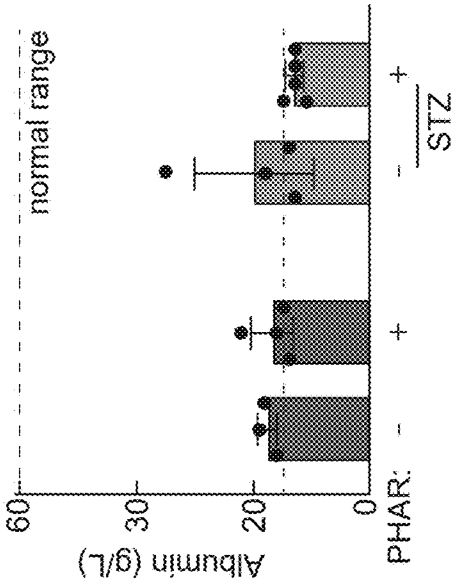
Figure 10C:
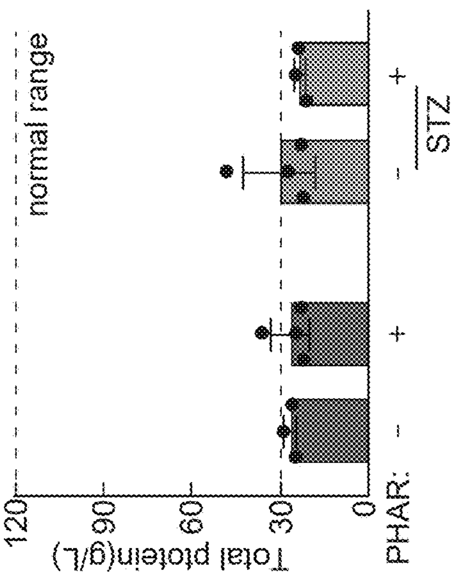
Figure 10D:
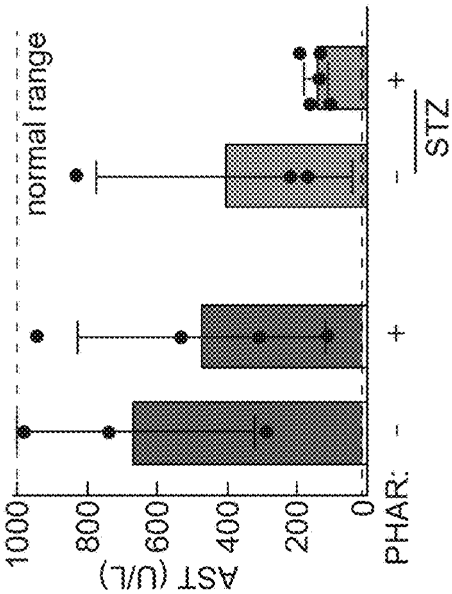
Figure 10E:
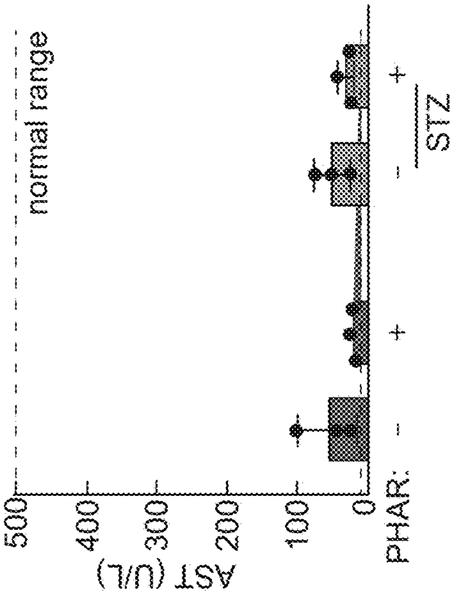

Preliminary safety studies have been performed in 7-week-old control and streptozotocin (STZ)-treated mice. These mice were subjected to an I.P treatment of 50 mg/kg of vehicle (Tween-80: PBS, 1:13) or PHAR for 4 weeks with 5 weekly doses. As seen in FIG. 10A, the mice did not lose weight during treatment, despite the fact that weight loss is a very sensitive indicator of disease in mice. On the other hand, serum levels of albumin, total protein and two transaminases (AST and ALT) were analyzed. As shown in FIG. 10B-E, these parameters showed values within normal ranges after 4 weeks. Therefore, toxicity data previously obtained in cell culture (FIG. 4H) together with these preliminary toxicological data obtained in mice suggest that prolonged administration of PHAR is safe.

Example 1.8. PHAR Reduces Inflammatory Response in LPS-Treated Mice

Figures 11A, 11B, 11C:
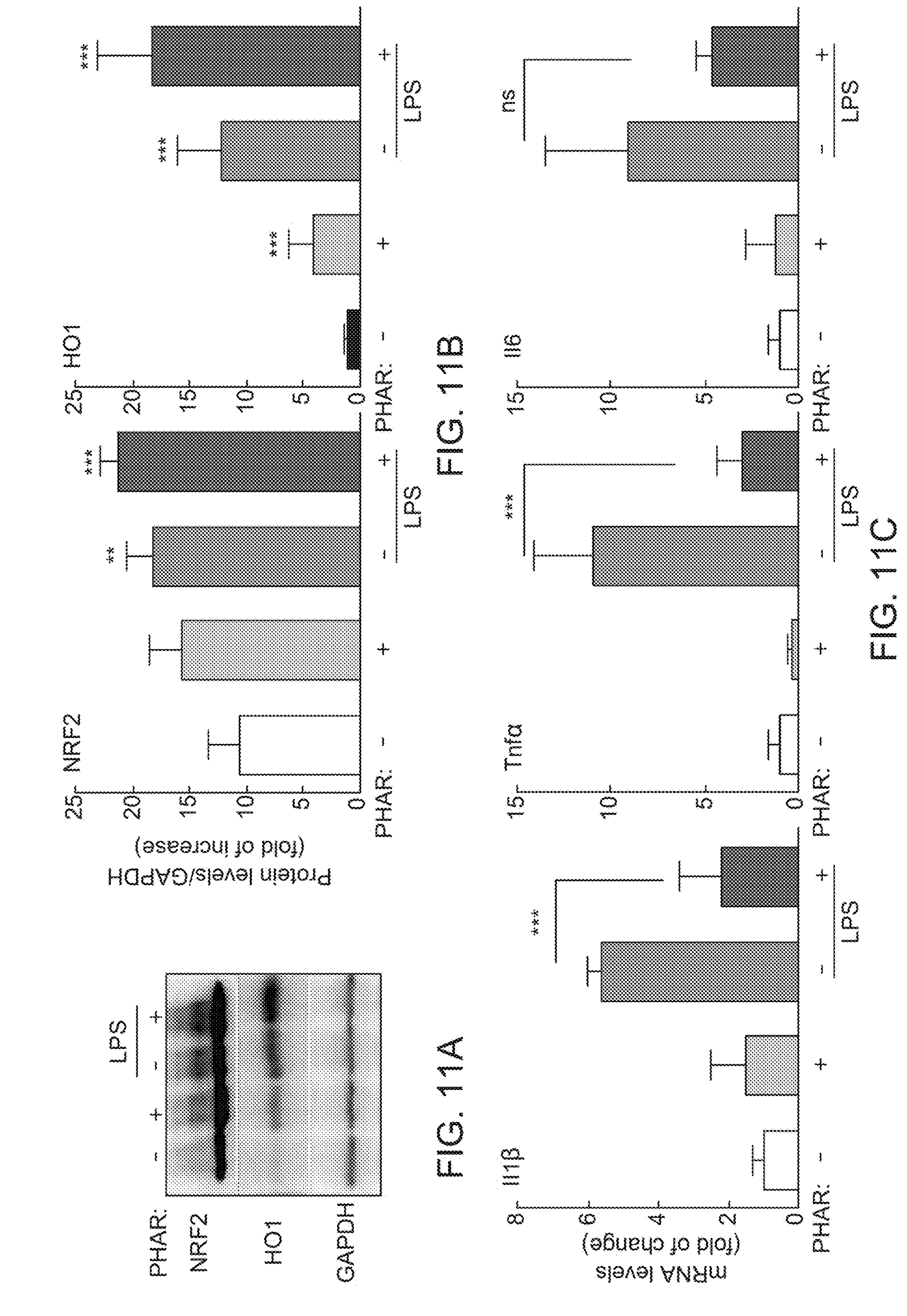
FIG. 11. PHAR reduces the inflammatory response in LPS-treated mice. The mice were divided into 4 experimental groups (n=4). Experimental groups 1 and 3 were treated by IP route with vehicle (Tween-80+PBS, 1:13) and experimental groups 2 and 4 with 50 mg/kg of PHAR for 5 days. After the second-to-last administration of the compound, groups 3 and 4 were treated by IP route with 1 mg/kg of LPS for 24 h. Two hours after the last dose of PHAR and twenty-four hours after the administration of LPS, all the mice were sacrificed by extracting the liver protein and total RNA, A), representative immunoblots showing NRF2, HO1, and GAPDH protein levels as the liver extract loading control. B), densitometric analysis of NRF2 and HO1 protein levels of the representative immunoblots shown in (A), expressed as a ratio of NRF2/GAPDH or HO1/GAPDH. The data is depicted as means±SEM (n=4). Statistical analysis was performed with one-way ANOVA followed by the Bonferroni test to compare inter-group differences. p<0.01; *p<0.001 vs. vehicle. C), the mRNA levels of Il1β, Il6, and Tnfα were determined by means of qRT-PCR and normalized by means of average Gapdh, Tbp, and β-actin. The data is depicted as mean±SEM (n=4). Statistical analysis was performed with one-way ANOVA followed by the Bonferroni test to check inter-group differences. ***p<0.001 vs. LPS. D) Representative images of hematoxylin and eosin (H&E) staining of mouse liver and immunohistochemical F4/80 staining of inflammatory liver macrophages (Kupffer cells). Note the reduction in F4/80 staining in the LPS+PHAR-treated mice compared to LPS-treated mice.
Figure 11D:
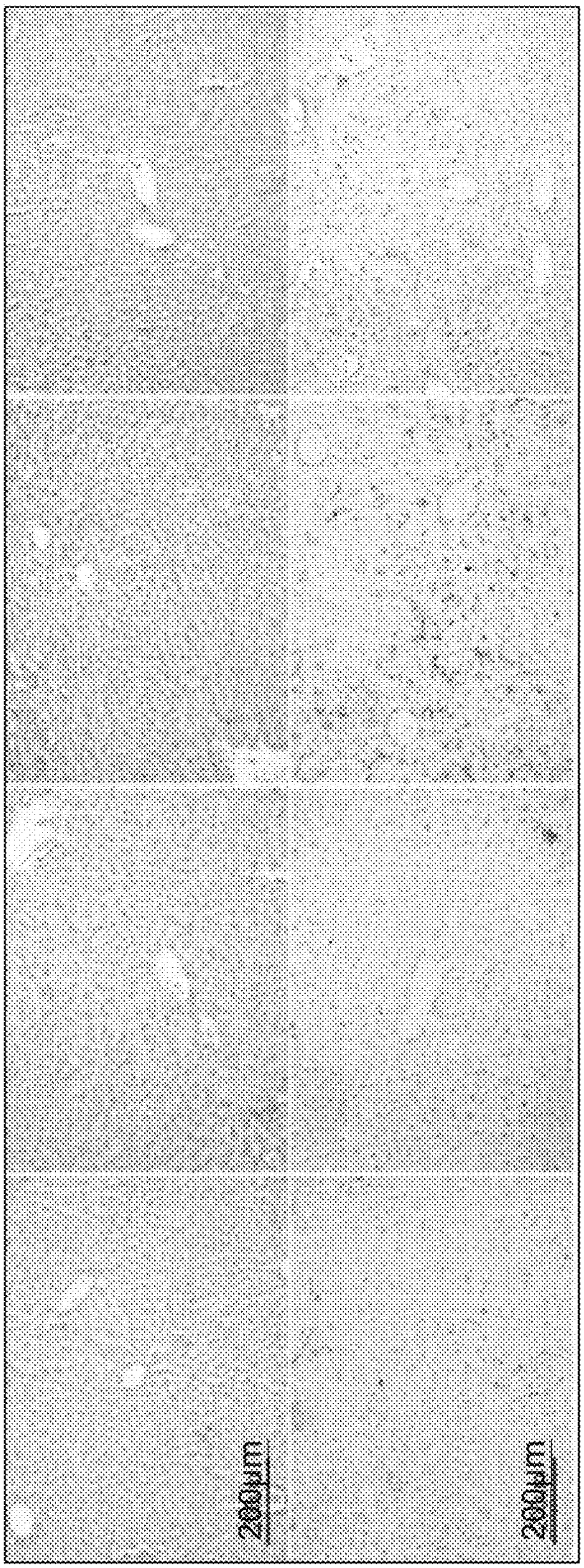

Once the in vitro anti-inflammatory effects of PHAR and its capacity to increase NRF2 and HO-1 levels in a model in vivo were demonstrated, it was evaluated whether the compound was capable of inhibiting LPS-mediated signaling in a murine model. To that end, 16 wild-type C57BL/6 mice were divided into 4 experimental groups: vehicle (experimental group 1), PHAR (experimental group 2), LPS (3), and LPS+PHAR (4). After obtaining results as promising as those described in detail in Example 1.6, the inventors decided to carry out the same experimental protocol. Briefly, the mice were treated daily by IP route with 50 mg/kg of PHAR (experimental groups 2 and 4) or vehicle (groups 1 and 3). Two hours after the second-to-last administration, experimental groups 3 and 4 were treated by IP route with 1 m/kg of LPS. Lastly, the last dose of PHAR was administered on the last day and 24 h after the administration of LPS, all the mice were sacrificed by extracting the liver protein and total RNA. Liver tissue protein analysis showed an increase in NRF2 levels derived from treatment with PHAR with a synergistic effect when treatment was performed with PHAR+LPS (FIGS. 11A and 11B). The clearest result was obtained when analyzing its target HO-1, where induction mediated by the compound could be clearly seen, and the same synergistic effect was again observed with combined treatment (FIGS. 11A and 11B). The analysis of the mRNA levels of different pro-inflammatory cytokines (Il1β, Il6, and Tnfα) showed a significant increase as a result of treatment with LPS, as expected. In this context, prior treatment with PHAR favored a significant reduction in the production of said cytokines (FIG. 11C). The histochemical analysis, using H&E, revealed that the liver structure remains unaltered with the PHAR treatment, further supporting a safety profile. Furthermore, immunohistochemical staining of the inflammatory activation of hepatic macrophages (Kupffer cells) by anti-F4/80 immunostaining revealed that LPS significantly activates these macrophages, as expected, and that this activation is greatly attenuated with PHAR treatment. Therefore, these obtained results confirm that treatment with PHAR favors an environment which protects against inflammation in mice in response to LPS.

Figure 12A:
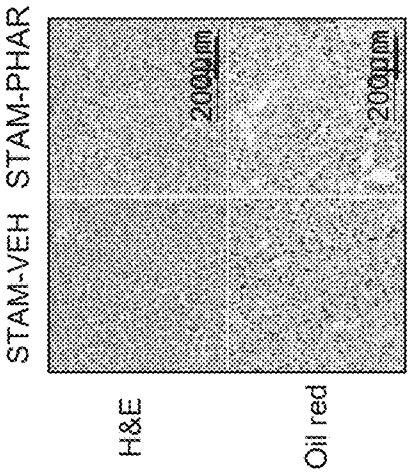
FIG. 12. PHAR decreases the inflammatory response in mice subjected to fatty liver in the STAM model. The STAM model is based on the induction of non-alcoholic fatty liver (NAFLD) generated by the subcutaneous injection of streptozotocin (STZ) in neonatal C57BL/6J mice (2-5 days old) followed by a high-fat diet administered from 4 weeks of age. In this case, we treated mice in the steatosis stage (week 6), 5 days a week with an IP administration of 50 mg/kg in order to analyze if PHAR prevents progression to the next stage (NASH). A), H&E staining of liver from PHAR-treated and untreated STAM mice. Histochemical lipid staining with oil red was used to visualize the amount of liver fat. B), normalized quantification of the amount of liver fat per mouse, measured by MRI, on the last day of treatment. C), representative MRI profiles of one mouse liver of each group. The peak that appears at an approximate frequency of 4.7 ppm corresponds to the water molecule (the majority), while the rest of the peaks give information on the amount of liver fat. The ratio of the sum of the fat peaks to water indicates the total liver fat content. D), mRNA levels of several genes involved in fatty acid metabolism (Cpt1a, Scd1, Cd36 and Fasn). E), the mRNA levels of the pro-inflammatory (Tnf, Il6 and Infg) and anti-inflammatory (Il10 and Il4) cytokines were determined by qRT-PCR and were normalized by the average of Gapdh, Tbp and β-actin. Statistical analysis was performed using a Student's t test to compare the differences between PHAR-treated mice vs vehicle-treated mice. *$p<0.05$; **$p<0.01$.
Figure 12B:
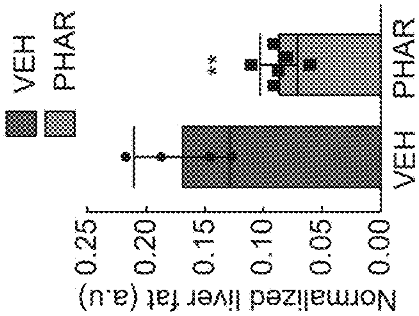
Figure 12C:
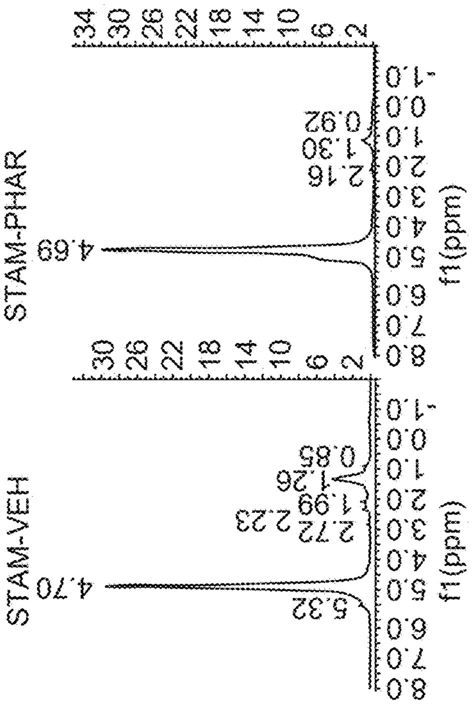
Figure 12D:
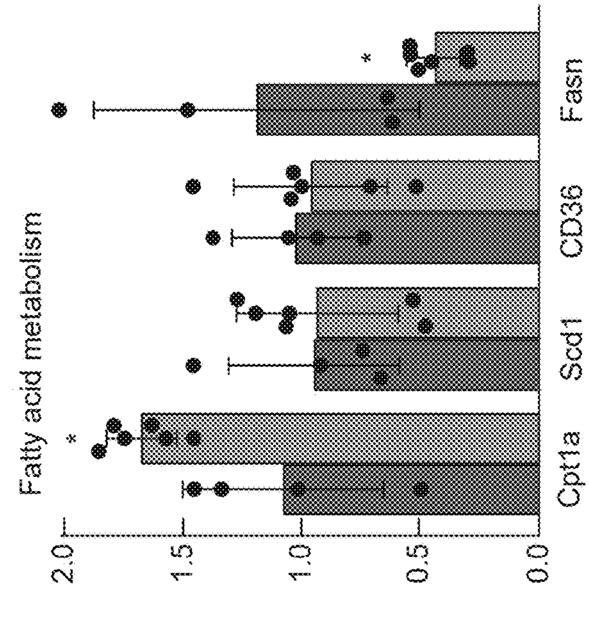
Figure 12E:
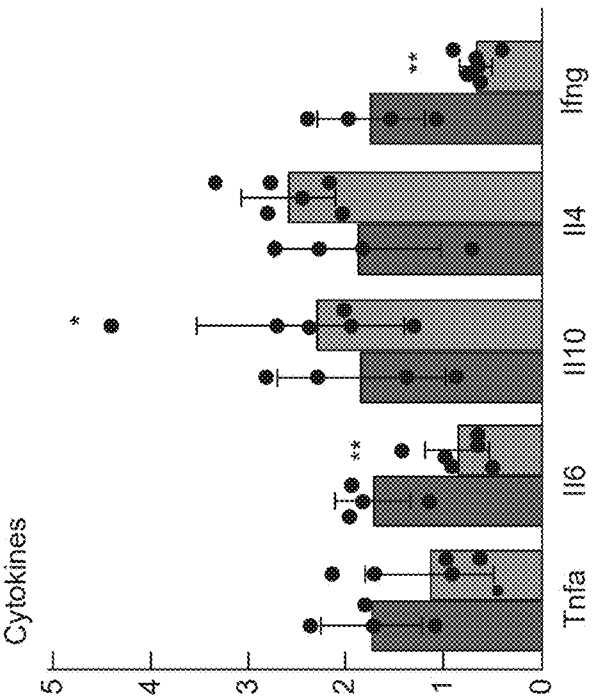

Example 1.9. PHAR Decreases the Inflammatory Response and Lipogenesis in STAM Mice Undergoing Fatty Liver Disease As previously described, the STAM model is a murine model used for the study of non-alcoholic fatty liver disease (NAFLD), as well as for the search of new effective treatments. This model is generated by the subcutaneous injection of streptozotocin (STZ) in 2-5 day old neonatal C57BL/6J mice followed by a high-fat diet, administered after 4 weeks of age. STZ produces a pancreatic lesion that leads to the appearance of hyperglycemia that, together with the high-fat diet, gradually leads to different stages of progressive liver damage: steatosis (week 6 post-STZ injection); Inflammatory NASH (week 8); NASH fibrosis (week 10) and, finally, hepatocarcinoma (week 16). The pathogenesis of NAFLD is closely related to the appearance of reactive oxygen species, chronic low-grade inflammation, and changes in lipid metabolism. For this reason, we determined whether PHAR, as an inducer of NRF2, could attenuate the inflammatory response. Specifically, we treated mice in the steatosis stage (week 6), 5 days a week with an IP administration of 50 mg/kg in order to analyze if it prevents progression to the next stage (NASH). As shown in FIG. 12A, H&E staining evidenced that the liver structure was similar in PHAR-treated and untreated STAM mice. On the other hand, lipid histochemistry using oil red showed accumulation of liver fat, corroborating the proper functioning of the model. In this case, PHAR significantly decreased the amount of accumulated liver fat. Analysis of liver fat quantity, measured by MRI at the end of treatment, revealed that PHAR slows the accumulation of liver fat in the STAM model (FIG. 12B-C). We analyzed the mRNA levels of various genes involved in fatty acid metabolism and found that PHAR produces a metabolic change consistent with the increase in lipid catabolism, evident in the expression of Cpt1a (carnitine palmitoyl transferase I) that facilitates the mitochondrial degradation of fatty acids, and in the decrease in their synthesis, by decreasing of Fasn (fatty acid synthase) expression (FIG. 12D). Finally, PHAR showed in the liver a tendency to decrease the expression of the pro-inflammatory cytokines Tnf, i16 and Infg and to increase the anti-inflammatory cytokines Il10 and Il4 (FIG. 12E). Altogether, we conclude that PHAR slows down the accumulation of fat and, therefore, prevents the appearance of NASH.

Example 1.10. PHAR Attenuates Liver Damage in Mice with Fatty Liver

Figure 13A:
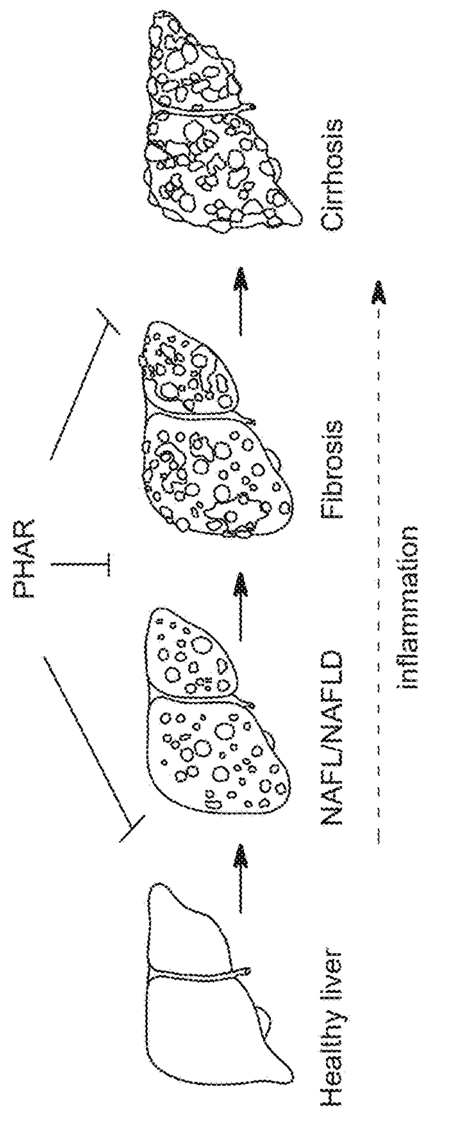
FIG. 13. PHAR slows fatty liver progression. The progressive damage of liver cells as a consequence of their metabolic alteration and chronic low-grade inflammation leads to their progression towards fibrosis and the consequent loss of liver function. The present invention makes it possible to treat patients diagnosed with fatty liver to prevent its progression towards more severe forms of liver disease such as fibrosis and cirrhosis. A) Scheme of the liver damage progression model. B) Representative spectra derived from MRI studies. At starting point (week 8; W8, NASH inflammation), mice subjected to the STAM protocol had fatty liver imitating the status of newly diagnosed patients. At this point, treatment with PHAR (50 mg/kg i.p; 5 days per week) began until week 10 (W10, fibrosis). C) standardized quantification of the amount of liver fat per mouse measured by MRI. Statistical analysis was performed using a two-way ANOVA followed by a Bonferroni test to compare the differences between treatments in control and STAM groups. **$p<0.01$. D) profiles of evolution of the amount of liver fat per mouse measured by MRI at week 8 (NASH) and week 10 (fibrosis). E) H&E histochemical analysis of mice treated with PHAR vs vehicle in control mice and in STAM mice together with oil red staining for determination of liver fat levels. F) levels of transcripts corresponding to the metabolism of fatty acids (Cpt1a, Scd1, Cd36 and Fasn). G) Levels of transcripts corresponding to pro-inflammatory cytokines (Tnf, Il6 and Infg) and anti-inflammatory (Il10 and Il4). For F and G, relative mRNA levels were determined by qRT-PCR and normalized by averaging Gapdh, Tbp, and β-actin. Statistical analysis was performed using a bidirectional ANOVA followed by a Bonferroni test to compare the differences between PHAR-treated mice vs vehicle-treated mice in the control and STAM models. *$p<0.05$; ***$p<0.001$.
Figure 13C:
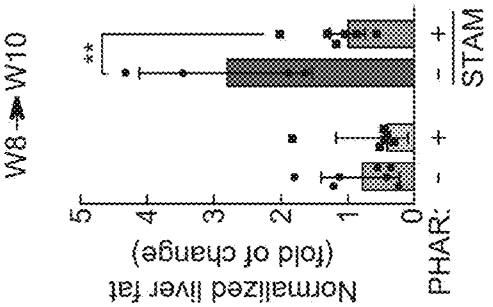
Figure 13B:
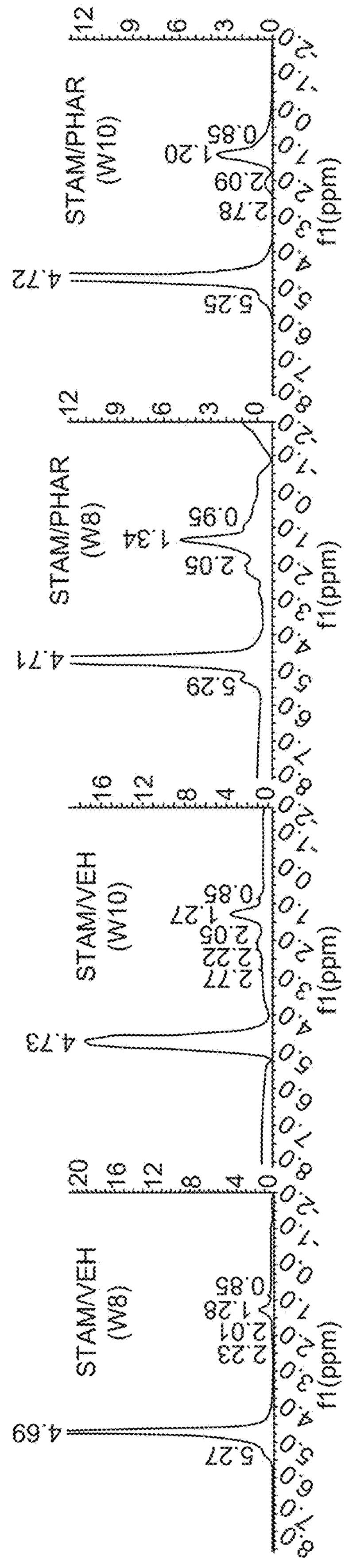
Figure 13D:
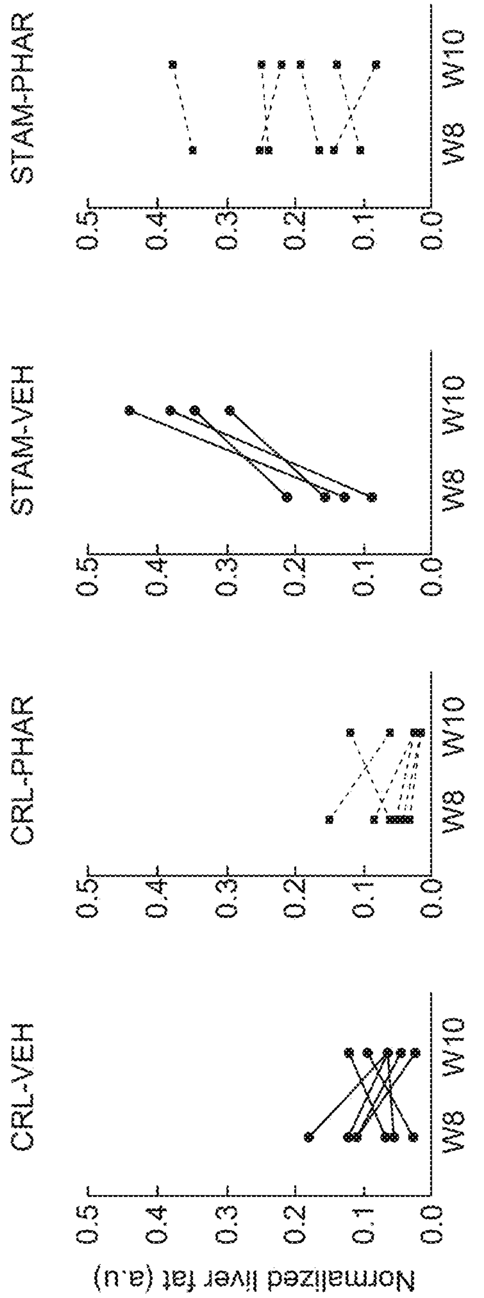
Figure 13E:
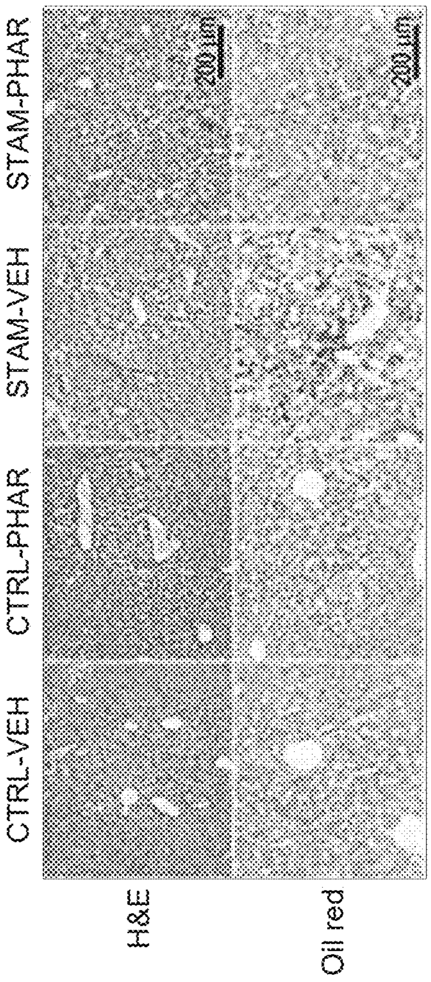
Figure 13F:
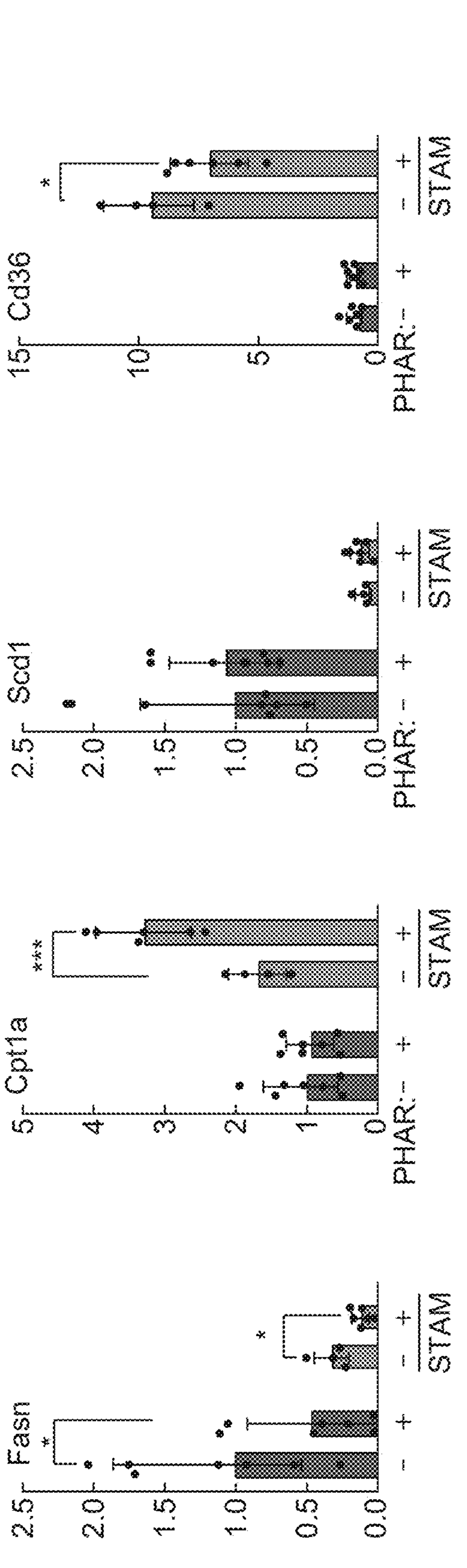
Figure 13G:
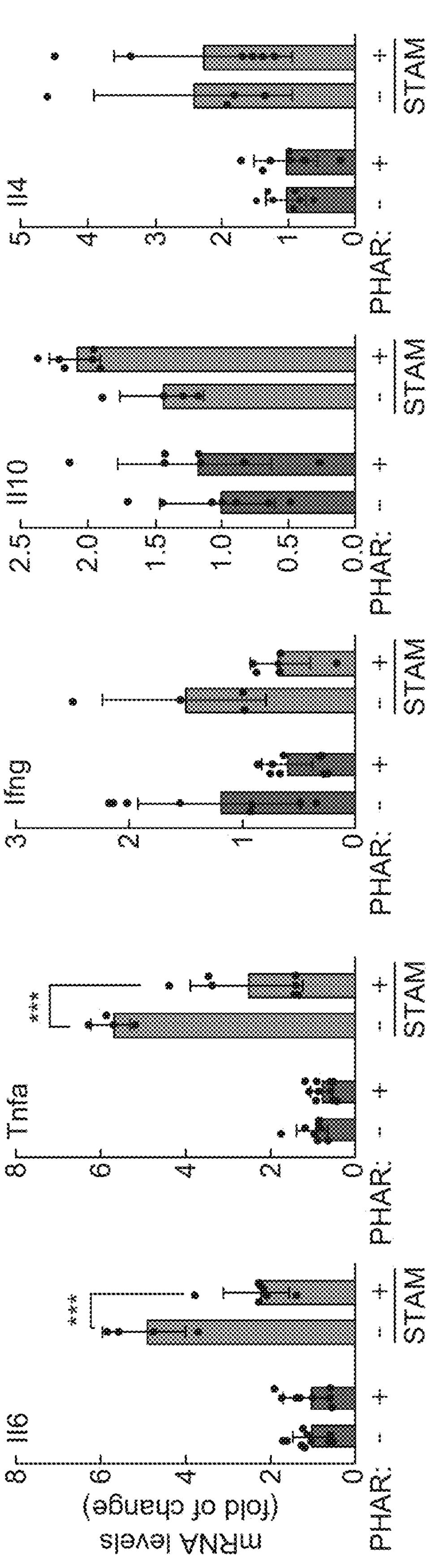

After seeing the beneficial role of PHAR in the prevention of NASH, we analyzed its role in progression of liver damage. The progressive damage of hepatocytes is a consequence of their metabolic alteration and chronic low-grade inflammation and oxidative stress (FIG. 13A). We treated mice in the NASH stage (week 8), 5 days a week with an IP dose of 50 mg/kg PHAR until week 10. The analysis of fat accumulation was measured by MRI both at the initial point of treatment and at the end point (FIG. 13B). Vehicle-treated STAM mice underwent a progressive accumulation of lipids. However, the mice treated with PHAR showed significant protection against lipid accumulation. As expected, the control mice did not suffer such fat accumulation, confirming the correct development of the STAM model (FIG. 13B-D). H&E histochemical analysis of liver from PHAR vs vehicle treated mice in both control and STAM mice confirmed again normal liver histology with treatment. Furthermore, oil red staining confirmed MRI results regarding protection against liver fat accumulation in STAM mice treated with PHAR (FIG. 13E). Consistent with the result obtained in example 1.9, PHAR produced an increase in lipid catabolism, increasing the expression of Cpt1a (carnitine palmitoyl transferase) and a decrease in its synthesis, measured by a decrease in the expression of Fasn (fatty acid synthase) (FIG. 16F). Analysis of the mRNA levels further indicates that PHAR attenuates the expression of pro-inflammatory cytokines and promotes an increase in anti-inflammatory cytokines (FIG. 16G). Therefore, PHAR reduces low-grade chronic inflammation and liver fat accumulation.

The invention claimed is:

1. An NRF2-βTrCP interaction inhibitor, characterized by Formula (I) or its derivative salts,

I

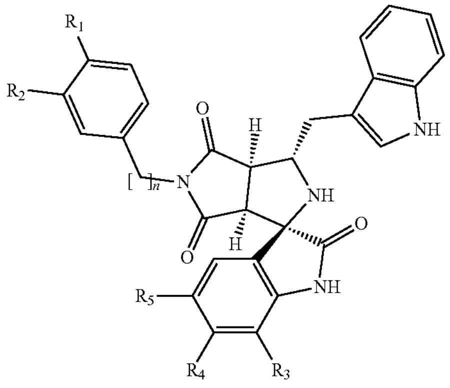

wherein:

n can be 0 or 1, $R_1$ can be $O_2CCH_3$ or a six-membered ring for forming a benzodioxane, benzomethylenedioxy, or naphthalene substituent;

$R_2$ can be H or a six-membered ring for forming a benzodioxane, benzomethylenedioxy, or naphthalene substituent;

$R_3$ can be H or $CH_3$;

$R_4$ can be H or $CH_3$; and $R_5$ can be H, Cl, or $CH_3$ for use in the treatment of fatty liver disease.

2. The NRF2-βTrCP interaction inhibitor for use according to claim 1, wherein the inhibitor is characterized by Formula (II),

II

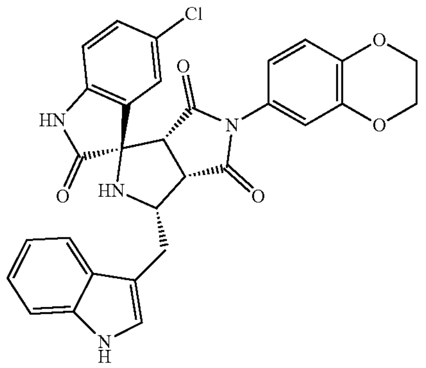

or its derivative salts.

3. A pharmaceutical composition comprising the NRF2-βTrCP interaction inhibitor of claim 1, or derivative salts thereof, and optionally pharmaceutically acceptable vehicles or excipients, for use in the treatment of fatty liver disease.

* * * * *